United States Patent
Zhang et al.

(10) Patent No.: US 11,945,935 B2
(45) Date of Patent: Apr. 2, 2024

(54) HYDROPHILIC POLYMER COMPOSITIONS

(71) Applicant: Saint-Gobain Performance Plastics Corporation, Solon, OH (US)

(72) Inventors: Jianfeng Zhang, Shrewsbury, MA (US); Jian L. Ding, Stow, MA (US); Guangyu Lu, Tewksbury, MA (US); Rachel Pytel, Newton, MA (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 807 days.

(21) Appl. No.: 16/870,554

(22) Filed: May 8, 2020

(65) Prior Publication Data

US 2020/0354546 A1 Nov. 12, 2020

Related U.S. Application Data

(60) Provisional application No. 62/845,286, filed on May 8, 2019.

(51) Int. Cl.
| | |
|---|---|
| *C08L 1/28* | (2006.01) |
| *A61L 15/22* | (2006.01) |
| *A61L 15/60* | (2006.01) |
| *A61L 29/04* | (2006.01) |
| *A61L 29/06* | (2006.01) |
| *A61L 29/14* | (2006.01) |
| *C08J 3/00* | (2006.01) |
| *C08J 3/075* | (2006.01) |
| *C08L 83/04* | (2006.01) |

(52) U.S. Cl.
CPC ............. *C08L 1/286* (2013.01); *A61L 15/225* (2013.01); *A61L 15/60* (2013.01); *A61L 29/041* (2013.01); *A61L 29/043* (2013.01); *A61L 29/049* (2013.01); *A61L 29/06* (2013.01); *A61L 29/145* (2013.01); *C08J 3/005* (2013.01); *C08J 3/075* (2013.01); *C08L 83/04* (2013.01); *C08J 2301/28* (2013.01); *C08J 2383/07* (2013.01); *C08J 2429/04* (2013.01); *C08J 2439/06* (2013.01); *C08J 2483/07* (2013.01); *C08L 2205/025* (2013.01); *C08L 2205/03* (2013.01); *C08L 2205/035* (2013.01)

(58) Field of Classification Search
CPC ...... A61L 15/225; A61L 29/041; A61L 29/06; A61L 29/145
See application file for complete search history.

(56) References Cited

U.S. PATENT DOCUMENTS

| | | | |
|---|---|---|---|
| 3,872,038 A | 3/1975 | Adams | |
| 5,362,833 A * | 11/1994 | Chen | C08K 5/17 528/10 |
| 5,639,413 A | 6/1997 | Crivello | |
| 8,273,802 B2 * | 9/2012 | Laredo | C08F 265/10 526/279 |
| 9,211,678 B2 | 12/2015 | DeSimone | |
| 2008/0138386 A1 | 6/2008 | Joffre | |
| 2008/0255492 A1 | 10/2008 | Truelsen | |
| 2010/0305231 A1 | 12/2010 | Kennedy | |
| 2012/0123054 A1 * | 5/2012 | Matsumoto | C08K 3/22 524/786 |
| 2012/0136323 A1 | 5/2012 | Stasko | |
| 2013/0101633 A1 | 4/2013 | Loewenhielm | |
| 2014/0131908 A1 | 5/2014 | Sun | |
| 2016/0024316 A1 * | 1/2016 | Sasada | C08L 71/02 252/512 |
| 2016/0223836 A1 | 8/2016 | Havenstrite | |
| 2016/0244625 A1 | 8/2016 | Clapp | |
| 2017/0066185 A1 | 3/2017 | Ermoshkin | |
| 2017/0283655 A1 | 10/2017 | Kenney | |
| 2018/0237659 A1 | 8/2018 | Kim | |
| 2018/0303866 A1 | 10/2018 | Brown | |
| 2019/0061236 A1 | 2/2019 | Rantala | |
| 2020/0048461 A1 | 2/2020 | Kobayashi | |

FOREIGN PATENT DOCUMENTS

| | | |
|---|---|---|
| CN | 104721875 A | 6/2015 |
| WO | 2016134972 A1 | 9/2016 |
| WO | 2019067604 A | 4/2019 |
| WO | 2019068093 A | 4/2019 |
| WO | 2019133947 A | 7/2019 |

OTHER PUBLICATIONS

International Search Report and Written Opinion in PCT/US2020/032181, dated Aug. 26, 2020.

* cited by examiner

*Primary Examiner* — Andrew S Rosenthal
(74) *Attorney, Agent, or Firm* — McDonnell Boehnen Hulbert & Berghoff LLP

(57) ABSTRACT

The present disclosure relates to methods for preparing a hydrophilic composition including intimately mixing a silicone component including at least one polysiloxane and a polymer component, and to hydrophobic polymer compositions prepared thereby. One aspect of the disclosure provides an article having a major exterior surface, the article comprising an intimate mixture of a silicone component including at least one polysiloxane; and a polymer component including at least one hydrophilic polymer having a water-absorption capacity of at least 50 wt. %; wherein the silicone component and the polymer component are present in the mixture in a dry weight ratio within the range of 99.9:0.1 to 30:70. In certain desirable embodiments as otherwise described herein, the intimate mixture is disposed at an exterior surface of the article, e.g., at the major exterior surface of the article.

27 Claims, 2 Drawing Sheets

HYDROPHILIC POLYMER COMPOSITIONS

CROSS-REFERENCE TO RELATED APPLICATIONS

This application claims the benefit of priority of U.S. Provisional Patent Application No. 62/845,286, filed May 8, 2019, which is hereby incorporated herein by reference in its entirety.

BACKGROUND OF THE DISCLOSURE

Field of the Disclosure

This disclosure relates generally to hydrophilic polymer compositions. More particularly, the present disclosure relates to methods for preparing a hydrophilic composition including intimately mixing a silicone component including at least one polysiloxane and a polymer component, and to hydrophobic polymer compositions prepared thereby.

Technical Background

Silicones, also known as polysiloxanes, are polymers made up of repeating siloxane units ($-SiR_2-O-$) in which each R can be any of a wide variety of substituents. Silicones are widely used in industry because silicone articles can be non-toxic, flexible, transparent, and thermally stable. Moreover, silicones can have low chemical reactivity, and silicone articles can be produced in a variety of shapes and sizes. For example, silicone tubing is popular in industries including medicine, pharmaceuticals, and food delivery.

However, many silicones are hydrophobic, and accordingly are unsuitable for certain applications. For example, proteins can accumulate on the surface of silicone tubing used for food delivery. Conventionally, surface modification (e.g., grafting) can provide a hydrophilic silicone surface, but the process is complicated, requires solvent, and can be difficult to reproduce consistently. And conventional methods for blending silicone with a hydrophobic component fail to provide desirable optical and mechanical properties. For example, certain blends of silicone and hydrophilic additives (e.g., modified polysiloxanes) are relatively opaque and brittle.

Accordingly, there remains a need for a method for preparing a hydrophilic polymer composition that can provide silicone-containing compositions having desirable optical and mechanical properties such as transparency and flexibility.

SUMMARY OF THE DISCLOSURE

In one aspect, the disclosure provides an article having a major exterior surface, the article comprising an intimate mixture of a silicone component including at least one polysiloxane; and a polymer component including at least one hydrophilic polymer having a water-absorption capacity of at least 50 wt. %; wherein the silicone component and the polymer component are present in the mixture in a dry weight ratio within the range of 99.9:0.1 to 30:70. In certain desirable embodiments as otherwise described herein, the intimate mixture is disposed at an exterior surface of the article, e.g., at the major exterior surface of the article.

In another aspect, the disclosure provides a method for preparing a hydrophilic polymer composition, the method comprising intimately mixing a silicone component including at least one polysiloxane; and a polymer component including at least one hydrophilic polymer having a water-absorption capacity of at least 50 wt. %; wherein the silicone component and the polymer component are present in the composition in a dry weight ratio within the range of 99.9:0.1 to 30:70.

Other aspects of the disclosure will be apparent to the person of ordinary skill in the art in view of the disclosure herein.

DETAILED DESCRIPTION

Figure 1:
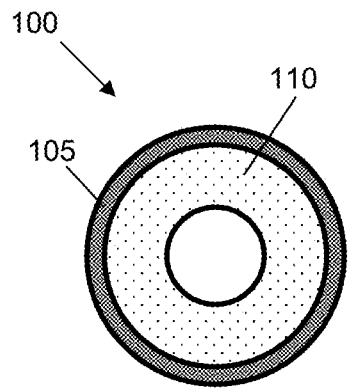
FIG. 1 is a cross-sectional schematic view of an article according to one embodiment of the disclosure.

The disclosure relates to hydrophilic polymer compositions that include a silicone component and a polymer component. In various advantageous aspects and embodiments as otherwise described herein, the hydrophilic polymer composition comprises an intimate mixture of a silicone component including at least one polysiloxane and a polymer component including at least one hydrophilic polymer. The disclosure demonstrates that such silicone-containing compositions can advantageously be hydrophilic and can further have desirable optical and mechanical properties. Accordingly, in certain advantageous embodiments, the intimate mixture is disposed at an exterior surface of the article, e.g., the major exterior surface of the article.

One aspect of the disclosure is a method for preparing a hydrophilic polymer composition. The method comprises intimately mixing a silicone component including at least one polysiloxane and a polymer component including at least one hydrophilic polymer having a water absorption capacity of at least 50 wt. %. The silicone component and the polymer component are present in the composition in a dry weight ratio (i.e., silicone component:polymer component) within the range of 99.9:1 to 30:70.

As used herein, the "water-absorption capacity" of a hydrophilic polymer describes the weight of water that can be absorbed by a polymer (i.e., fully submerged in water) at equilibrium, at 23° C., per unit weight of the hydrophilic polymer. For example, the water-absorption capacity of microcrystalline cellulose at 23° C. is 53.5 wt. %.

As used herein, each individual component of an "intimate mixture" maybe be entirely incorporated into the mixture (i.e., indiscernible on a nanometer scale), or may comprise discrete nanometer- or micron-scale domains dispersed throughout the mixture. For example, in certain embodiments as otherwise described herein, the silicone component and the polymer component each individually comprise domains having a major dimension of less than 1 mm (e.g., less than 200 µm, or less than 100 µm, or less than 50 µm).

In certain embodiments as otherwise described herein, the silicone component comprises a cross-linkable polysiloxane, present in the silicone component in an amount within the range of 10 wt. % to 99.9 wt. %, and an effective amount of a cross-linking agent (i.e., an amount effective to cause cross-linking of the polysiloxane to provide a substantially cross-linked material).

The silicone component includes one or more polysiloxanes that can be polymerized (i.e., cross-linked) to provide a composition of larger compounds. Moreover, when a chemical substance described herein is referenced in the singular, it is to be understood that such substance (especially when in polymeric form) will contain a distribution of individual molecules having somewhat different characteristics. Accordingly, structural attributes described herein are understood to be on average, on a per-molecule basis. Moreover, even when a chemical substance is described in the singular, it is understood that such description pertains to multiple such substances in combination. Accordingly, "a polysiloxane having at least about two alkenyl groups" refers not only to a material having on average at least about two alkenyl groups per molecule, but also combinations of materials each having on average at least about two alkenyl groups per molecule. In certain embodiments, "at least about two" of any moiety described herein is at least 1.90, at least 1.95, or even at least 1.98 of that moiety per molecule on average. And "about two" of a moiety means, in certain embodiments, in the range of 1.90-2.10, or 1.95-2.05 or 1.98-2.02 of that moiety per molecule on average.

For example, in certain such embodiments, the cross-linkable polysiloxane is present in the silicone component in an amount within the range of 5 wt. % to 99.9 wt. %, or 10 wt. % to 99.9 wt. %, or 15 wt. % to 99.9 wt. %, or 20 wt. % to 99.9 wt. %, or 25 wt. % to 99.9 wt. %, or 30 wt. % to 99.9 wt. %, or 35 wt. % to 99.9 wt. %, or 40 wt. % to 99.9 wt. %, or 45 wt. % to 99.9 wt. %, or 50 wt. % to 99.9 wt. %, or 55 wt. % to 99.9 wt. %, or 60 wt. % to 99.9 wt. %, or 65 wt. % to 99.9 wt. %, or 70 wt. % to 99.9 wt. %, or 75 wt. % to 99.9 wt. %, or 80 wt. % to 99.9 wt. %, or 5 wt. % to 95 wt. %, or 5 wt. % to 90 wt. %, or 5 wt. % to 85 wt. %, or 5 wt. % to 80 wt. %, or 5 wt. % to 75 wt. %, or 5 wt. % to 70 wt. %, or 5 wt. % to 65 wt. %, or 5 wt. % to 60 wt. %, or 5 wt. % to 55 wt. %, or 5 wt. % to 50 wt. %, or 5 wt. % to 45 wt. %, or 5 wt. % to 40 wt. %, or 5 wt. % to 35 wt. %, or 5 wt. % to 30 wt. %, or 5 wt. % to 25 wt. %, or 10 wt. % to 30 wt. %, or 15 wt. % to 35 wt. %, or 20 wt. % to 40 wt. %, or 25 wt. % to 45 wt. %, or 30 wt. % to 50 wt. %, or 35 wt. % to 55 wt. %, or 40 wt. % to 60 wt. %, or 45 wt. % to 65 wt. %, or 50 wt. % to 70 wt. %, or 55 wt. % to 75 wt. %, or 60 wt. % to 80 wt. %, or 65 wt. % to 85 wt. %, or 70 wt. % to 90 wt. %, or 75 wt. % to 95 wt. %, or 80 wt. % to 98 wt. %.

In certain embodiments as otherwise described herein, the cross-linkable polysiloxane comprises one or more groups selected from alkenyl groups and silicon hydride groups, and the cross-linking agent comprises a thermally active initiator. In certain embodiments as otherwise described herein, the thermally active initiator is selected from di-aralkyl peroxides, alkyl-aralkyl peroxides, and di-alkyl peroxides, such as, for example, dicumyl peroxide, or bis(2,4-dichlorobenzoyl)peroxide. In certain embodiments as otherwise described herein, the thermally active initiator is a hydrosilylation catalyst such as, for example, a platinum hydrosilylation catalyst. In certain such embodiments, the hydrosilylation can be thermally active and also photoactive.

In certain embodiments as otherwise described herein, the thermally active initiator is present in the silicone component in an amount within the range of 0.05 wt. % to 10 wt. %. For example, in certain such embodiments, the thermally active initiator is present in the silicone component in an amount within the range of 0.05 wt. % to 9 wt. %, or 0.05 wt. % to 8 wt. %, or 0.05 wt. % to 7 wt. %, or 0.05 wt. % to 6 wt. %, or 0.05 wt. % to 5 wt. %, or 0.05 wt. % to 4 wt. %, or 0.05 wt. % to 3 wt. %, or 0.05 wt. % to 2 wt. %, or 0.1 wt. % to 8 wt. %, or 0.1 wt. % to 6 wt. %, or 0.5 wt. % to 5 wt. %, or 0.5 wt. % to 4 wt. %, or 0.5 wt. % to 2 wt. %.

In certain embodiments as otherwise described herein, the cross-linking agent comprises an initiator (e.g., a photo- or thermally active initiator) and a cross-linker such as, for example, a polysiloxane, siloxane, or silane cross-linker. For example, in certain such embodiments, the cross-linkable polysiloxane comprises at least about two alkenyl groups, and the cross-linking agent comprises a hydrosilylation catalyst and a siloxane cross-linker comprising about two silicon hydride groups.

In another example, in certain embodiments as otherwise described herein, the cross-linkable polysiloxane comprises one or more hydroxyl groups, and the cross-linking agent comprises a condensation catalyst and a cross-linker comprising one or more groups selected from alkoxy, acetoxy, ester, enoxy and oxime groups. For example, in certain embodiments as otherwise described herein, the condensation catalyst comprises tin. In certain such embodiments, the cross-linker comprises a silane comprising at least about two alkoxy groups or acetoxy groups, such as, for example, methyl trimethoxy silane or methyl triacetoxysilane.

In certain embodiments as otherwise described herein, the number-average molecular weight of the cross-linkable polysiloxane is within the range of about 25 kDa to about 1 MDa. For example, in certain embodiments as otherwise described herein, the molecular weight of cross-linkable polysiloxane is within the range of about 50 kDa to about 1 MDa, or about 75 kDa to about 1 MDa, or about 100 kDa to about 1 MDa, or about 150 kDa to about 1 MDa, or about 200 kDa to about 1 MDa, or about 300 kDa to about 1 MDa, or about 400 kDa to about 1 MDa, or about 500 kDa to about 1 MDa, or about 600 kDa to about 1 MDa, or about 700 kDa to about 1 MDa, or about 25 kDa to about 900 kDa, or about 25 kDa to about 800 kDa, or about 25 kDa to about 700 kDa, or about 25 kDa to about 600 kDa, or about 25 kDa to about 500 kDa, or about 25 kDa to about 400 kDa, or about 25 kDa to about 300 kDa, or about 25 kDa to about 250 kDa, or about 25 kDa to about 200 kDa, or about 25 kDa to about 150 kDa, or about 25 kDa to about 100 kDa, or about 50 kDa to about 900 kDa, or about 100 kDa to about 800 kDa, or about 200 kDa to about 700 kDa, or about 300 kDa to about 600 kDa.

In certain embodiments as otherwise described herein, the viscosity of the cross-linkable polysiloxane (i.e., at 25° C.) is at least 2,000 cP. For example, in certain such embodiments, the viscosity of the cross-linkable polysiloxane is within the range of 10,000 cP to 1,000,000 cP. In another example, in certain such embodiments, the viscosity of the cross-linkable polysiloxane is greater than 1,000,000 cP, or greater than 10,000,000 cP, or greater than 50,000,000 cP.

In certain embodiments as otherwise described herein, the silicone component comprises a first polysiloxane having at least about one silicon hydride group, a second polysiloxane having at least about one alkenyl group, and an effective amount of a hydrosilylation catalyst (i.e., an amount effective to cause hydrosilylation of alkenyl groups to provide a substantially polymerized material). In certain such embodiments, the first polysiloxane and the second polysiloxane comprise at least 30 wt. %, or at least 40 wt. %, or at least 50 wt. % of the silicone component.

In certain embodiments as otherwise described herein, the first polysiloxane comprises about two silicon hydride groups. For example, in certain such embodiments, the first polysiloxane comprises tetramethyldisiloxane or hydride-terminated poly(dimethylsiloxane). In certain embodiments as otherwise described herein, the first polysiloxane comprises about three or more silicon hydride groups. For example, in certain such embodiments, the first polysiloxane comprises trimethylsiloxane-terminated poly(methylhydrosiloxane) or trimethylsiloxane-terminated poly(methylhydrosiloxane)-poly(dimethylsiloxane) copolymer. In certain embodiments as otherwise described herein, the first polysiloxane comprises a number of silicon hydride groups within the range of about 5 to about 1,000, or about 10 to about 1,000, or about 50 to about 1,000, or about 100 to about 1,000, or about 5 to about 500, or about 10 to about 500, or about 50 to about 500, or about 100 to about 500, or about 5 to about 100, or about 10 to about 100, or about 50 to about 100, or about 3 to about 100, or about 3 to about 50, or about 3 to about 20.

In certain embodiments as otherwise described herein, one or more alkenyl groups of the second polysiloxane is independently a terminal alkenyl group. In certain such embodiments, each alkenyl group is independently a terminal alkenyl group. For example, in certain embodiments as otherwise described herein, one or more (e.g., each) alkenyl group of the second polysiloxane is independently selected from a but-3-enyl group, an allyl group, or a vinyl group.

In certain embodiments as otherwise described herein, one or more alkenyl groups of the second polysiloxane is independently a non-terminal alkenyl group. In certain such embodiments, each alkenyl group is independently a non-terminal alkenyl group. For example, in certain embodiments as otherwise described herein, one or more (e.g., each) alkenyl group is independently selected from a prop-1-enyl group or a but-2-enyl group.

In certain embodiments as otherwise described herein, the second polysiloxane comprises about two alkenyl groups. In other embodiments, the second polysiloxane comprises 3 or more alkenyl groups. For example, in certain such embodiments, the polysiloxane comprises a number of alkenyl groups within the range of 3 to 1,000, or 3 to 750, or 3 to 500, or 3 to 500, or 3 to 400, or 3 to 300, or 3 to 200, or 5 to 1,000, or 25 to 1,000, or 50 to 1,000, or 100 to 1,000, or 250 to 1,000, or 500 to 1,000, or 5 to 200, or 100 to 300, or 200 to 400, or 300 to 500, or 400 to 600, or 500 to 700, or 600 to 800, or 700 to 900.

In certain embodiments as otherwise described herein, the number of siloxane repeat units of the second polysiloxane comprising an alkenyl group is within the range of 0.001% to 10% of the total number of siloxane repeat units. For example, in certain such embodiments, the number of siloxane repeat units comprising an alkenyl group is within the range of 0.001% to 9%, or 0.001% to 8%, or 0.001% to 7%, or 0.001% to 6%, or 0.001% to 5%, or 0.001% to 4%, or 0.001% to 3%, or 0.001% to 2%, or 0.001% to 1%, or 0.005% to 5%, or 0.01% to 4.5%, or 0.05% to 4%, or 0.1% to 3.5%, or 0.15% to 3%, or 0.2% to 3%, or 0.25% to 3%, or 0.5% to 3%. In other embodiments, the number of siloxane repeat units of the second polysiloxane comprising an alkenyl group is within the range of 2% to 20% of the total number of siloxane repeat units. For example, in certain embodiments as otherwise described herein, the number of siloxane repeat units comprising an alkenyl group is within the range of 2% to 18%, or 2% to 16%, or 2% to 14%, or 2% to 12%, or 2% to 10%, or 2% to 8%, or 2% to 6%, or 4% to 20%, or 6% to 20%, or 8% to 20%, or 10% to 20%, or 12% to 20%, or 14% to 20%, or 16% to 20%, or 4% to 10%, or 6% to 12%, or 8% to 14%, or 10% to 16%, or 12% to 18%.

In certain embodiments as otherwise described herein, the at least about two alkenyl groups are provided as pendant groups from internal siloxanes of the second polysiloxane. In certain such embodiments, the polysiloxane comprises a vinyl-pendant polysiloxane, e.g., a vinylmethylsiloxane homopolymer, a vinylmethylsiloxane-dimethylsiloxane copolymer, a vinylmethylsiloxane-dimethylsiloxane-(meth)acryloyloxypropylmethyl siloxane terpolymer, etc.

In certain embodiments as otherwise described herein, the at least about two alkenyl groups are provided at ends of the second polysiloxane. For example, in certain such embodiments, the second polysiloxane comprises a vinyl-terminated polysiloxane, e.g., a vinyl-terminated (meth)acryloyloxypropylmethyl homopolymer, a vinyl-terminated (meth)acryloyloxypropylmethyl-dimethylsiloxane copolymer, etc.

In certain embodiments as otherwise described herein, the at least about two alkenyl groups are provided as a combination of at one or more ends of the second polysiloxane and as pendant groups from one or more internal siloxanes of the second polysiloxane. For example, in certain such embodiments, the second polysiloxane comprises a vinyl-terminated, vinyl-pendant polysiloxane, e.g., a vinyl-terminated vinylmethylsiloxane-(meth)acryloyloxypropyl methyl siloxane copolymer, a vinyl-terminated vinylmethylsiloxane-dimethylsiloxane-(meth)acryloyloxypropylmethyl siloxane terpolymer, etc.

In certain embodiments as otherwise described herein, the molar ratio of silicon hydride groups present in the silicone component to alkenyl groups present in the silicone component is within the range of 3:2 to 2:3, or within the range of 5:4 to 4:5, or within the range of 9:8 to 8:9. Of course, one or more polysiloxanes present in the silicone component can comprise alkenyl groups, and one or more polysiloxanes present in the composition can comprise silicon hydride groups.

For example, in certain such embodiments, the first polysiloxane is present in the silicone component in an amount within the range of 0.05 wt. % to 40 wt. %, and the second polysiloxane is present in the silicone component in an amount within the range of 2 wt. % to 99.95 wt. %. In certain such embodiments, the first siloxane (e.g., having at least about two silicon hydride groups) is present in the silicon component in an amount within the range of 0.1 wt. % to 40 wt. %, or 0.5 wt. % to 40 wt. %, or 1 wt. % to 40 wt. %, or 2.5 wt. % to 40 wt. %, or 5 wt. % to 40 wt. %, or 10 wt. % to 40 wt. %, or 15 wt. % to 40 wt. %, or 20 wt. % to 40 wt. %, 0.05 wt. % to 35 wt. %, or 0.05 wt. % to 30 wt. %, or 0.05 wt. % to 25 wt. %, or 0.05 wt. % to 20 wt. %, or 0.05 wt. % to 15 wt. %, or 0.05 wt. % to 10 wt. %, or 0.1 wt. % to 30 wt. %, or 0.1 wt. % to 20 wt. %, or 0.25 wt. % to 17.5 wt. %, or 0.25 wt. % to 15 wt. %, or 0.5 wt. % to 10 wt. %. In certain such embodiments, the second siloxane (e.g., having at least about two alkenyl groups) is present in the silicon component in an amount within the range of 2.5 wt. % to 99.95 wt. %, or 5 wt. % to 99.95 wt. %, or 7.5 wt. % to 99.95 wt. %, or 10 wt. % to 99.95 wt. %, or 15 wt. % to 99.95 wt. %, or 20 wt. % to 99.95 wt. %, or 30 wt. % to 99.95 wt. %, or 40 wt. % to 99.95 wt. %, or 50 wt. % to 99.95 wt. %, or 60 wt. % to 99.95 wt. %, or 2 wt. % to 99.5 wt. %, or 2 wt. % to 99 wt. %, or 2 wt. % to 95 wt. %, or 2 wt. % to 90 wt. %, or 2 wt. % to 85 wt. %, or 2 wt. % to 80 wt. %, or 2 wt. % to 70 wt. %, or 2 wt. % to 60 wt. %, or 2 wt. % to 50 wt. %, or 2 wt. % to 40 wt. %, or 5 wt. % to 99.9 wt. %, or 10 wt. % to 99.9 wt. %, or 15 wt. % to 99.9 wt. %, or 20 wt. % to 99.9 wt. %, or 25 wt. % to 95 wt. %, or 30 wt. % to 90 wt. %, or 35 wt. % to 85 wt. %.

In another example, in certain such embodiments, the first polysiloxane is present in the silicone component in an amount within the range of 0.1 wt. % to 80 wt. %, and the second polysiloxane is present in the silicone component in an amount within the range of 2 wt. % to 99.9 wt. %. In certain such embodiments, the first siloxane (e.g., having at least about two silicon hydride groups) is present in the silicon component within the range of 0.1 wt. % to 75 wt. %, or 0.1 wt. % to 70 wt. %, or 0.1 wt. % to 65 wt. %, or 0.1 wt. % to 60 wt. %, or 0.1 wt. % to 55 wt. %, or 0.1 wt. % to 50 wt. %, or 0.1 wt. % to 45 wt. %, or 0.1 wt. % to 40 wt. %, or 0.5 wt. % to 80 wt. %, or 1 wt. % to 80 wt. %, or 2.5 wt. % to 80 wt. %, or 5 wt. % to 80 wt. %, or 10 wt. % to 80 wt. %, or 15 wt. % to 80 wt. %, or 20 wt. % to 80 wt. %, or 30 wt. % to 80 wt. %, or 40 wt. % to 80 wt. %, or 0.5 wt. % to 70 wt. %, or 1 wt. % to 60 wt. %, or 2.5 wt. % to 50 wt. %, or 5 wt. % to 40 wt. %. In certain such embodiments, the second siloxane (e.g., having at least about two alkenyl groups) is present in the silicon component in an amount within the range of 2.5 wt. % to 99.9 wt. %, or 5 wt. % to 99.9 wt. %, or 7.5 wt. % to 99.9 wt. %, or 10 wt. % to 99.9 wt. %, or 15 wt. % to 99.9 wt. %, or 20 wt. % to 99.9 wt. %, or 30 wt. % to 99.9 wt. %, or 40 wt. % to 99.9 wt. %, or 50 wt. % to 99.95 wt. %, or 60 wt. % to 99.95 wt. %, or 2 wt. % to 99.5 wt. %, or 2 wt. % to 99 wt. %, or 2 wt. % to 95 wt. %, or 2 wt. % to 90 wt. %, or 2 wt. % to 85 wt. %, or 2 wt. % to 80 wt. %, or 2 wt. % to 70 wt. %, or 2 wt. % to 60 wt. %, or 2 wt. % to 50 wt. %, or 2 wt. % to 40 wt. %, or 5 wt. % to 99.9 wt. %, or 10 wt. % to 99.9 wt. %, or 15 wt. % to 99.9 wt. %, or 20 wt. % to 99.9 wt. %, or 25 wt. % to 95 wt. %, or 30 wt. % to 90 wt. %, or 35 wt. % to 85 wt. %.

In certain embodiments as otherwise described herein, the hydrosilylation catalyst is a photoactive catalyst. In other embodiments, the hydrosilylation catalyst is a thermally active catalyst. For example, in certain embodiments as otherwise described herein, the hydrosilylation catalyst is a photo- or thermally active catalyst comprising one or more platinum group metals (i.e., platinum, rhodium, ruthenium, palladium, osmium, and iridium). In certain embodiments as otherwise described herein, the hydrosilylation catalyst is a platinum catalyst. For example, in certain such embodiments, the hydrosilylation catalyst is a thermally activated platinum catalyst such as, for example, Karstedt's catalyst (platinum(0)-1,3-divinyl-1,1,3,3-tetramethyldisiloxane) or Speier's catalyst ($H_2PtCl_6$). In another example, in certain such embodiments, the hydrosilylation is a photoactive platinum catalyst such as, for example platinum bis(β-diketonates) (e.g., Pt(acetylacetonate)$_2$, Pt(hexafluoroacetylacetone), Pt(PPh$_3$)$_2$Cl$_2$), η$^5$-cyclopentadienyl trimethyl platinum(IV) complexes, or platinum-triazenido complexes.

In certain embodiments as otherwise described herein, the hydrosilylation catalyst is a supported hydrosilylation catalyst comprising, for example, a platinum-group metal on the surface of a carbon, silica, or alumina solid support. In certain such embodiments, the hydrosilylation catalyst is platinum on carbon, palladium on carbon, ruthenium on carbon, rhodium on carbon, platinum on silica, palladium on silica, platinum on alumina, palladium on alumina, or ruthenium. In certain embodiments, the hydrosilylation is an encapsulated catalyst comprising, for example, a platinum-group metal encapsulated in a resin (e.g., a thermoplastic resin).

In certain embodiments as otherwise described herein, the hydrosilylation catalyst is present in the silicone component in an effective amount, for example, within the range of 0.0001 wt. % to 1 wt. %. In certain such embodiments, the hydrosilylation catalyst is present in the silicone component in an amount within the range of 0.0001 wt. % to 0.9 wt. %, or 0.0001 wt. % to 0.8 wt. %, or 0.0001 wt. % to 0.7 wt. %, or 0.0001 wt. % to 0.6 wt. %, or 0.0001 wt. % to 0.5 wt. %, or 0.0001 wt. % to 0.4 wt. %, or 0.0001 wt. % to 0.3 wt. %, or 0.0001 wt. % to 0.2 wt. %. For example, in certain embodiments as otherwise described herein, the silicone component comprises a first polysiloxane having at least about one (e.g., at least about two) silicone hydride group, present in an amount within the range of 0.1 wt. % to 20 wt. %, a second polysiloxane having at least about one (e.g., at least about two) alkenyl group, present in the silicone component in an amount within the range of 20 wt. % to 99.9 wt. %, and a hydrosilylation catalyst (e.g., a photo- or thermally active platinum catalyst) present in an amount within the range of 0.0001 wt. % to 0.2 wt. %. In another example, in certain embodiments as otherwise described herein, the silicone component comprises a first polysiloxane having at least about one (e.g., at least about two) silicone hydride group, present in an amount within the range of 1 wt. % to 60 wt. %, a second polysiloxane having at least about one (e.g., at least about two) alkenyl group, present in the silicone component in an amount within the range of 20 wt. % to 99.9 wt. %, and a hydrosilylation catalyst (e.g., a photo- or thermally active platinum catalyst) present in an amount within the range of 0.0001 wt. % to 0.2 wt. %.

In certain embodiments as otherwise described herein, one or more polysiloxanes of the silicone component comprises at least about one reactive heterocycloalkyl group. Advantageously, the present inventors have determined that heterocycloalkyl groups reactive towards a functional group of one or more hydrophilic polymers (e.g., an alcohol group of one or more polysaccharides) can form cross-links between polysiloxanes of the silicone component and one or more hydrophilic polymers (e.g., one or more polysaccharides) of the polymer component. Accordingly, in certain embodiments as otherwise described herein, the silicone component comprises one or more polysiloxanes having at least about one reactive heterocycloalkyl group, present in the silicone component in an amount within the range of 0.05 wt. % to 99.95 wt. %.

In certain embodiments as otherwise described herein, the silicone component includes one or more polysiloxanes comprising at least about one (e.g., at least about two) reactive heterocycloalkyl groups. In certain embodiments as otherwise described herein, each reactive heterocycloalkyl group is a cyclic ether. For example, in certain such embodiments, each reactive group is an epoxide group or an oxetane group. In certain embodiments as otherwise described herein, the polysiloxane comprises about two reactive heterocycloalkyl groups. For example, in certain embodiments as otherwise described herein, the second polysiloxane comprises 1,3-bis(3-(2,3-epoxypropoxy)propyl)tetramethyldisiloxane or 3-(2,3-epoxypropoxy)propyl-terminated poly(dimethylsiloxane). In certain embodiments as otherwise described herein, the polysiloxane comprises about three or more heterocycloalkyl groups. For example, in certain embodiments as otherwise described herein, the polysiloxane comprises trimethylsiloxane-terminated poly((3-(2,3-epoxypropoxy)propyl)methylsiloxane)-poly(dimethylsiloxane) copolymer. In certain embodiments as otherwise described herein, the polysiloxane comprises about two succinic anhydride groups. For example, in certain embodiments as otherwise described herein, the polysiloxane comprises succinic anhydride-terminated poly(dimethylsiloxane). In certain embodiments as otherwise described herein, the polysiloxane comprises a number of reactive heterocycloalkyl groups within the range of about 5 to about 500, or about 10 to about 500, or about 50 to about 500, or about 100 to about 500, or about 5 to about 100, or about 10 to about 100, or 20 to about 100, or about 3 to about 50, or about 5 to about 50, or about 10 to about 50, or about 3 to about 20 or about 5 to about 20 or about 100 to about 500.

In certain embodiments as otherwise described herein, the silicone component further comprises one or more inhibitors. A variety of inhibitors are known in the art, such as, for example, amines (e.g., ammonia, ethyl amine, di- and trialkyl amines) and inert dyes. In certain embodiments as otherwise described herein, the silicone component comprises one or more inhibitors in an amount within the range of 0.002 wt. % to 1 wt. %, or 0.002 wt. % to 0.9 wt. %, or 0.002 wt. % to 0.8 wt. %, or 0.002 wt. % to 0.7 wt. %, or 0.002 wt. % to 0.6 wt. %, or 0.002 wt. % to 0.5 wt. %, or 0.002 wt. % to 0.4 wt. %, or 0.002 wt. % to 0.3 wt. %, or 0.002 wt. % wt. % to 0.2 wt. %, or 0.005 wt. % to 0.15 wt. %, or 0.005 wt. % to 0.1 wt. %, or 0.005 wt. % to 0.075 wt. %, or 0.005 wt. % to 0.05 wt. %.

In certain embodiments as otherwise described herein, the silicone component further comprises one or more particulate fillers. A variety of fillers are known in the art, such as, for example, ceramic particles, glass particles, metallic particles, polymeric particles, or a combination thereof. For example, in certain such embodiments, the filler is selected from of silicon dioxide ($SiO_2$) compounds, such as fumed silica (i.e., amorphous silica having particle size of about 5-50 nm and a surface area of about 50-600 $m^2/g$), silica fume (or micro silica; i.e., amorphous silica having particle size of less than 1 μm, with average about 150 nm, and a surface area of about 15-30 $m^2/g$), fused quartz (or fused silica), perlite (i.e., an amorphous volcanic glass, which is mostly silica with some aluminum oxide), diatomaceous earth (i.e., silica rock having an average particle size of 10-200 μm), fly ash (i.e., coal combustion byproduct comprising amorphous and crystalline silica, $Al_2O_3$, $Fe_2O_3$, and CaO), slag or slag cement (i.e., byproduct of metal smelting comprising a mixture of silica and metal oxides), alumina, ceria, magnesium-magnesia aluminate (MMA), magnesium oxide, silicon nitride, silicon carbide, hydroxyapatite, cordierite, soda-lime glass, low iron glass, borosilicate glass, or a combination thereof. In certain such embodiments, the silicone component comprises fumed silica. In certain embodiments as otherwise described herein, the silicone component includes a non-reactive polysiloxane filler, or a mono-functional reactive polysiloxane filler.

The filler can have any suitable particle size, e.g., the longest dimension of the particle, such as the average longest dimension. For example, in certain embodiments as otherwise described herein, the filler has a primary particle size of about 5 nm to about 100 nm, about 10 to about 30 nm, or about 5 nm or less, or about 50 nm or more, or about 100 nm or more. As used herein, "primary" particle size refers to the actual particles in their unagglomerated state, which can optionally agglomerate to form larger "secondary" particles.

In certain embodiments as otherwise described herein, the silicone component comprises a filler in an amount up to about 70 wt. %. In certain such embodiments, the polymerizable composition comprises a filler in an amount within the range of about 1 wt. % to 70 wt. %, or 2.5 wt. % to 70 wt. %, or 5 wt. % to 70 wt. %, or 10 wt. % to 70 wt. %, or 15 wt. % to 70 wt. %, or 20 wt. % to 70 wt. %, or 25 wt. % to 70 wt. %, or 30 wt. % to 70 wt. %, or 1 wt. % to 60 wt. %, or 1 wt. % to 50 wt. %, or 1 wt. % to 40 wt. %, or 1 wt. % to 30 wt. %, or 1 wt. % to 20 wt. %, or 10 wt. % to 30 wt. %, or 20 wt. % to 40 wt. %, or 30 wt. % to 50 wt. %, or 40 wt. % to 60 wt. %, or 50 wt. % to 70 wt. %. In certain such embodiments, the filler comprises silica (e.g., fumed silica) or titania. In certain such embodiments, the filler comprises silicone resin or a silsesquioxane. In certain such embodiments, the filler comprises one or more metal oxides (e.g., calcium oxide, zinc oxide, magnesium oxide).

In certain embodiments as otherwise described herein, the polysiloxanes, cross-linking agents, fillers, and inhibitors are present in a combined amount of at least 80 wt. % of the silicone component of the article. For example, in certain such embodiments, the polysiloxanes, cross-linking agents, fillers, and inhibitors are present in a combined amount of at least 90 wt. %, at least 95 wt. %, or at least 97.5 wt. % of the silicone component of the article.

In certain embodiments as otherwise described herein, the polymer component comprises a hydrophilic polymer having a water-absorption capacity of at least 60 wt. %, or at least 75 wt. %, or at least 85 wt. %, or at least 95 wt. %, or at least 100 wt. %. In certain embodiments as otherwise described herein, the at least one hydrophilic polymer includes polyvinyl alcohol or polyvinyl pyrrolidone, for example, in an amount within the range of 10 wt. % to 95 wt. %, or 30 wt. % to 95 wt. %, or 50 wt. % to 95 wt. %, or 70 wt. % to 95 wt. %, or 10 wt. % to 75 wt. %, or 10 wt. % to 55 wt. %, or 10 wt. % to 35 wt. %, or 20 wt. % to 85 wt. %, or 30 wt. % to 75 wt. % of the polymer component.

In certain embodiments as otherwise described herein, the at least one hydrophilic polymer includes a saccharide selected from oligosaccharides and polysaccharides, for example, in an amount within the range of 10 wt. % to 95 wt. %, or 30 wt. % to 95 wt. %, or 50 wt. % to 95 wt. %, or 70 wt. % to 95 wt. %, or 10 wt. % to 75 wt. %, or 10 wt. % to 55 wt. %, or 10 wt. % to 35 wt. %, or 20 wt. % to 85 wt. %, or 30 wt. % to 75 wt. % of the polymer component.

As used herein, oligosaccharides include linear or branched chains of about 3 to about 10 monosaccharides (e.g., glucose, arabinose, xylose, glucosamine, etc.). Further as used herein, polysaccharides include linear or branched chains of at least about 11 monosaccharides. Oligo- and polysaccharides include synthetic and naturally occurring oligo- and polysaccharides (e.g., fructooligosaccharide, cellulose, chitosan, etc.), and any derivative thereof such as, for example, cellulose derivatives including cellulose acetate propionate, cellulose acetate butyrate, cellulose nitrate, cellulose sulfate, methylcellulose, ethylcellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, carboxymethyl cellulose, and croscarmellose sodium. For the purposes of this disclosure, oligomeric and polymeric materials having at least 80 wt % saccharide residues are considered to be oligosaccharides and/or polysaccharides. Accordingly, copolymers with sorbitol residues such as the material commonly known as "polydextrose" are included within the definition of an oligosaccharide.

In certain embodiments as otherwise described herein, the at least one hydrophilic polymer includes an ionic polysaccharide. In certain embodiments as otherwise described herein, the hydrophilic polymer includes one or more polysaccharides selected from starch, alginate, cellulose, hyaluronic acid, chitin, and derivatives thereof.

The present inventors have determined that providing an intimate mixture of a silicone component as otherwise described herein with a polymer component comprising a hydrophilic polymer (e.g., a polysaccharide) and a liquid having a cellulose-swelling capacity of at least 20 wt. % can, advantageously, provide a hydrophilic polymer composition having desirable optical properties (e.g., transparency) and mechanical properties (e.g., flexibility, coefficient of friction). As used herein, the cellulose-swelling capacity of a liquid refers to the amount of the liquid that can be absorbed by cellulose at equilibrium, at 23° C., relative to the amount of cellulose. Of course, the hydrophilic polymer of the polymer component is not limited to cellulose; rather, cellulose absorption is used as a measure of the ability of a liquid to be absorbed by hydrophilic polymers. One or more hydrophilic polymers of such a polymer component can, in certain embodiments, be fully or partially dissolved in or swollen by the liquid, such that the liquid and the hydrophilic polymer provide a homogenous mixture. The person of ordinary skill in the art will appreciate that a mixture of a liquid having a cellulose-swelling capacity with a hydrophilic polymer can, based on the identities and relative amounts of the hydrophilic polymers and the liquid, be in the form of a paste, gum, suspension, swollen mass, etc., and that the liquid can be provided to the material during preparation of the material, or alternatively by absorption prior to or during use.

Accordingly, in certain embodiments as otherwise described herein, the polymer component includes a polyvinyl alcohol as a hydrophilic polymer and a liquid having a cellulose-swelling capacity of at least 20 wt. %. The liquid can be, for example, present in the polymer component in an amount within the range of 5 wt. % to 70 wt. % (e.g., within the range of 5 wt. % to 50 wt. %); and polyvinyl alcohol can be, for example, present in the polymer component in an amount within the range of 30 wt. % to 95 wt. % (e.g., within the range of 50 wt. % to 95 wt. %). In certain embodiments as otherwise described herein, the polymer component includes polyvinyl alcohol and a liquid having a cellulose-swelling capacity of at least 25 wt. %, or at least 50 wt. %, or at least 75 wt. %. In certain embodiments as otherwise described herein, the liquid comprises (e.g., is) methanol, ethanol, acetone, acetonitrile, or any mixture thereof. In certain embodiments as otherwise described herein, the liquid comprises (e.g., is) water.

In certain embodiments as otherwise described herein, the polymer component is a includes one or more saccharides (e.g., as described above, selected from oligosaccharides and polysaccharides) and a liquid having a cellulose-swelling capacity of at least 20 wt. %. The liquid can be, for example, present in the polymer component in an amount within the range of 5 wt. % to 70 wt. % (e.g., within the range of 5 wt. % to 50 wt. %); and the one or more saccharides can be, for example, present in the polymer component in a combined amount within the range of 30 wt. % to 95 wt. % (e.g., within the range of 50 wt. % to 95 wt. %).

In certain such embodiments, the one or more saccharides are present in the polymer component in a combined amount within the range of 30 wt. % to 90 wt. %, or 30 wt. % to 80 wt. %, or 30 wt. % to 70 wt. %, or 30 wt. % to 60 wt. %, or 30 wt. % to 55 wt. %, or 30 wt. % to 50 wt. %, or 40 wt. % to 95 wt. %, or 50 wt. % to 95 wt. %, or 60 wt. % to 95 wt. %, or 70 wt. % to 95 wt. %, or 40 wt. % to 60 wt. %, or 50 wt. % to 70 wt. %, or 60 wt. % to 80 wt. %. In certain such embodiments, the liquid is present in the polymer component in an amount within the range of 10 wt. % to 70 wt. %, or 20 wt. % to 70 wt. %, or 30 wt. % to 70 wt. %, or 40 wt. % to 70 wt. %, or 50 wt. % to 70 wt. %, or 5 wt. % to 60 wt. %, or 5 wt. % to 50 wt. %, or 5 wt. % to 40 wt. %, or 5 wt. % to 30 wt. %, or 5 wt. % to 20 wt. %, or 10 wt. % to 30 wt. %, or 20 wt. % to 40 wt. %, or 30 wt. % to 50 wt. %, or 40 wt. % to 60 wt. %, or 50 wt. % to 70 wt. %.

In certain embodiments as otherwise described herein, the polymer component comprises one or more polysaccharides selected from starch, alginate, cellulose, hyaluronic acid, and derivatives thereof. For example, in certain embodiments as otherwise described herein, the polymer component comprises cellulose or a cellulose derivative (e.g., carboxymethyl cellulose). In another example, in certain embodiments as otherwise described herein, the polymer component y comprises alginate. In another example, in certain embodiments as otherwise described herein, the polymer component comprises hyaluronic acid. In another example, in certain embodiments as otherwise described herein, the polymer component comprises starch.

In certain embodiments as otherwise described herein, the polymer component comprises a polysaccharide comprising 1,4-α-linked repeat units according to Formula I:

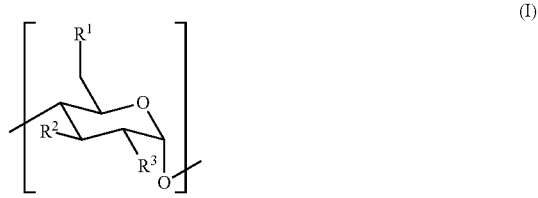

wherein each $R^1$ is selected from hydroxyl, —OR', —OC(O)R', —OR'', and an 1,6-α-linked repeat unit according to Formula I; $R^2$ and $R^3$ are each independently selected from —OR', —OC(O)R', and —OR''; each R' is independently selected from hydrogen and optionally substituted alkyl, cycloalkyl, heterocycloalkyl, aryl, and heteroaryl; and each R'' is independently selected from nitrate, sulfate, and phosphate.

In certain embodiments, $R^1$ of one or more repeat units of the polysaccharide is a repeat unit according to Formula I (i.e., forming a 1,6-α-linkage between repeat units). In certain embodiments, $R^1$ of one or more repeat units is selected from —OR', —OC(O)R', and —OR''. In certain such embodiments, $R^1$ of one or more repeat units is independently —OR' or —OC(O)R', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. In certain embodiments, $R^1$ of one or more repeat units is —OR', and each R' is independently hydrogen or alkyl (e.g., optionally substituted with a hydroxyl group). In certain embodiments, $R^1$ of one or more repeat units is —OC(O)R', and each $R^1$ is independently hydrogen or alkyl (e.g., optionally substituted with a hydroxyl group).

In certain embodiments, $R^2$ and $R^3$ of one or more repeat units are independently —OR' or —OC(O)R', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. In certain embodiments, $R^2$ and $R^3$ of one or more repeat units are —OR', and each R' is independently hydrogen or alkyl (e.g., optionally substituted with a hydroxyl group). In certain embodiments, $R^2$ of one or more repeat units is —OC(O)R' and each R' is independently hydrogen or alkyl (e.g., optionally substituted with a hydroxyl group). In certain such embodiments, $R^3$ of the one or more repeat units is —OH. In certain embodiments, $R^3$ of one or more repeat units is —OC(O)R', and each R' is independently hydrogen or alkyl (e.g., optionally substituted with a hydroxyl group). In certain such embodiments, $R^2$ of the one or more repeat units is —OH.

In certain embodiments, one or more (e.g., each) of $R^1$, $R^2$, and $R^3$ of one or more repeat units are —OR". In certain such embodiments, R" is nitrate. For example, in certain embodiments, each of $R^1$, $R^2$, and $R^3$ of one or more repeat units of the polysaccharide is nitrate.

In certain embodiments as otherwise described herein, the polymer component comprises a polysaccharide comprising 1,4β-linked repeat units according to Formulas II and

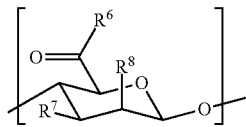

(II)

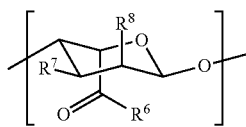

(III)

wherein each $R^6$ is independently selected from —OR', —OC(O)R', and —NHR'; $R^7$ and $R^8$ are each independently selected from —OR', and —OC(O)R', and —OR"; each R' is independently selected from hydrogen and optionally substituted alkyl, cycloalkyl, heterocycloalkyl, aryl, and heteroaryl; and each R" is independently selected from nitrate, sulfate, and phosphate.

In certain embodiments, the polysaccharide comprises homopolymeric blocks of 1,4-β-linked repeat units according to Formula II and homopolymeric blocks of 1,4β-linked repeat units according to Formula III, the homopolymeric blocks also 1,4β-linked. In certain embodiments, the polysaccharide comprises blocks of 1,4β-linked, alternating repeat units of Formula II and repeat units of Formula III.

In certain embodiments, $R^6$ of one or more repeat units of the polysaccharide is —NHR', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. For example, in certain such embodiments, $R^6$ of one or more repeat units of the polysaccharide is NHR', and R' is cycloalkyl or heterocycloalkyl, each optionally substituted with 1-2 oxo groups.

In certain embodiments, $R^7$ and $R^8$ of one or more repeat units are independently —OR' or —OC(O)R', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. In certain embodiments, $R^7$ and $R^8$ of one or more repeat units are —OR', and each R' is independently hydrogen or alkyl (e.g., optionally substituted with a hydroxyl group). In certain embodiments, $R^7$ of one or more repeat units is —OC(O)R' and each R' is independently hydrogen or alkyl (e.g., optionally substituted with a hydroxyl group). In certain such embodiments, $R^8$ of the one or more repeat units is —OH. In certain embodiments, $R^8$ of one or more repeat units is —OC(O)R', and each R' is independently hydrogen or alkyl (e.g., optionally substituted with a hydroxyl group). In certain such embodiments, $R^7$ of the one or more repeat units is —OH.

In certain embodiments, one or more (e.g., each) of $R^7$ and $R^8$ of one or more repeat units are —OR". In certain such embodiments, R" is nitrate. For example, in certain embodiments, each of $R^7$ and $R^8$ of one or more repeat units of the polysaccharide is nitrate.

In certain embodiments as otherwise described herein, the polymer component comprises a polysaccharide comprising 1,4-β-linked repeat units according to Formula IV:

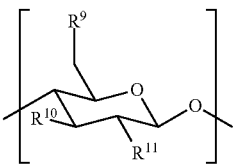

(IV)

wherein each $R^9$ is selected from hydroxyl, —OR', —OC(O)R', and —OR"; $R^{10}$ and $R^{11}$ are each independently selected from —OR', —OC(O)R', and —OR"; each R' is independently selected from hydrogen and optionally substituted alkyl, cycloalkyl, heterocycloalkyl, aryl, and heteroaryl; and each R" is independently selected from nitrate, sulfate, and phosphate.

In certain embodiments, $R^9$, $R^{10}$ and $R^{11}$ of one or more repeat units are independently —OR' or —OC(O)R', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. In certain embodiments, $R^9$, $R^{10}$, and $R^{11}$ of one or more repeat units are —OR', and each R' is independently hydrogen or alkyl (e.g., optionally substituted with a hydroxyl group). In certain embodiments, $R^9$ of one or more repeat units is —OC(O)R' and each R' is independently hydrogen or alkyl (e.g., optionally substituted with a hydroxyl group). In certain embodiments, $R^{10}$ of one or more repeat units is —OC(O)R' and each R' is independently hydrogen or alkyl (e.g., optionally substituted with a hydroxyl group). In certain such embodiments, $R^{11}$ of the one or more repeat units is —OH. In certain embodiments, $R^{11}$ of one or more repeat units is —OC(O)R', and each R' is independently hydrogen or alkyl (e.g., optionally substituted with a hydroxyl group). In certain such embodiments, $R^9$ and $R^{10}$ of the one or more repeat units are —OH.

In certain embodiments, one or more (e.g., each) of $R^9$, $R^{10}$, and $R^{11}$ of one or more repeat units are —OR". In certain such embodiments, R" is nitrate. For example, in certain embodiments, each of $R^9$, $R^{10}$, and $R^{11}$ of one or more repeat units of the polysaccharide is nitrate.

In certain embodiments as otherwise described herein, the polymer component comprises a polysaccharide comprising 1,4β-linked repeat units repeat units according to Formula V:

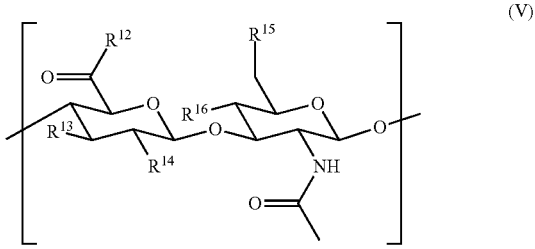

wherein each $R^{12}$ is independently selected from —OR', —OC(O)R', and —NHR'; $R^{13}$, $R^{14}$, $R^{15}$, and $R^{16}$ are each independently selected from —OR', and —OC(O)R', and —OR"; each R' is independently selected from hydrogen and optionally substituted alkyl, cycloalkyl, heterocycloalkyl, aryl, and heteroaryl; and each R" is independently selected from nitrate, sulfate, and phosphate.

In certain embodiments, $R^{12}$ of one or more repeat units of the polysaccharide is —NHR', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. For example, in certain such embodiments, $R^{12}$ of one or more repeat units of the polysaccharide is NHR', and R' is cycloalkyl or heterocycloalkyl, each optionally substituted with 1-2 oxo groups.

In certain embodiments, $R^{13}$, $R^{14}$, $R^{15}$, and $R^{16}$ of one or more repeat units are independently —OR' or —OC(O)R', and each R' is independently selected from optionally substituted (e.g., optionally substituted with 1-3 groups selected from hydroxyl, oxo, ether, thiol, thioether, amine, ester, amide, cyano, isocyanate, thioisocyanate, carbamate, epoxy, and halogen) alkyl, cycloalkyl, heterocycloalkyl, aryl, and heteroaryl. In certain embodiments, $R^{13}$, $R^{14}$, $R^{15}$, and $R^{16}$ of one or more repeat units are —OR', and each R' is independently hydrogen or alkyl (e.g., optionally substituted with a hydroxyl group).

In certain embodiments, one or more (e.g., each) of $R^{13}$, $R^{14}$, $R^{15}$, and $R^{16}$ of one or more repeat units are —OR". In certain such embodiments, R" is nitrate. For example, in certain embodiments, each of $R^{13}$, $R^{14}$, $R^{15}$, and $R^{16}$ of one or more repeat units of the polysaccharide is nitrate.

In certain embodiments as otherwise described herein, the polymer component comprises one or more ionically cross-linked polysaccharides. For example, in certain such embodiments, the polymer component comprises a $Ca^{2+}$-cross-linked polysaccharide such as, for example, $Ca^{2+}$-cross-linked carboxymethyl cellulose. In certain embodiments as otherwise described herein, the polymer component comprises one or more covalently cross-linked polysaccharides. For example, in certain such embodiments, the polymer component comprises one or more polysaccharides cross-linked by reaction of one or more hydroxyl groups (e.g., with a glutaraldehyde cross-linker), or by radical reactions (e.g., peroxide-initiated cross-linking). In other such embodiments, the polymer component comprises one or more polysaccharides cross-linked by addition reactions (e.g., with a 1,6-hexamethylenediisocyanate or 1,6-hexanedibromide cross-linker).

In certain embodiments as otherwise described herein, the molecular weight of one or more (e.g., each) oligo- or polysaccharide of the polymer component is at least 2,500 Da. In certain embodiments as otherwise described herein, the molecular weight of one or more (e.g., each) oligo- or polysaccharide of the polymer component is within the range of 16 kDa to 16 MDa. For example, in certain such embodiments, the molecular weight of one or more (e.g., each) oligo- or polysaccharide of the polymer component is within the range of 16 kDa to 12 MDa, or 16 kDa to 8 MDa, or 16 kDa to 4 MDa, or 16 kDa to 1 MDa, or 16 kDa to 800 kDa, or 16 kDa to 600 kDa, or 16 kDa to 400 MDa, or 16 kDa to 200 MDa, or 16 kDa to 100 kDa, or 25 kDa to 16 MDa, or 50 kDa to 16 MDa, or 100 kDa to 16 MDa, or 250 kDa to 16 MDa, or 500 kDa to 16 MDa, or 1 MDa to 16 MDa, or 4 MDa to 16 MDa, or 8 MDa to 16 MDa, or 12 MDa to 16 MDa, or 25 kDa to 250 kDa, or 100 kDa to 500 kDa, or 100 kDa to 1 MDa, or 500 kDa to 2 MDa, or 1 MDa to 4 MDa, or 2 MDa to 5 MDa, or 3 MDa to 8 MDa, or 4 MDa to 10 MDa, or 6 MDa to 12 MDa, or 8 MDa to 14 MDa.

Advantageously, the present inventors have determined that an oligo- or polysaccharide lacking siloxane functionality (i.e., as part of the polymer component) can be intimately mixed with a silicone component to provide a hydrophilic polymer composition further having desirable optical and mechanical properties. Of course, in other embodiments, the polymer component can include an oligo- or polysaccharide comprising a siloxane group.

In certain embodiments as otherwise described herein, the polymer component comprises a liquid having a cellulose-swelling capacity of at least 25 wt. %, or at least 50 wt. %, or at least 75 wt. %. In certain embodiments as otherwise described herein, the liquid comprises (e.g., is) methanol, ethanol, acetone, acetonitrile, or any mixture thereof. In certain embodiments as otherwise described herein, the liquid comprises (e.g., is) water.

For example, in certain embodiments as otherwise described herein, the polymer component comprises one or more polysaccharides, present in the polymer component in a total amount within the range of 10 wt. to 95 wt. %, and water, present in the polymer component in an amount within the range of 5 wt. % to 90 wt. %. In certain such embodiments, the polymer component comprises one or more polysaccharides, present in the polymer component in a total amount within the range of 30 wt. % to 70 wt. %, and water, present in the polymer component in an amount within the range of 30 wt. % to 70 wt. %.

Advantageously, the present inventors have determined that the methods as otherwise described herein can provide one or more hydrophilic polymers (e.g., one or more polysaccharides) exposed on a hydrated surface of the composition. In certain embodiments, one or more polysaccharides comprising the hydrophilic polymer composition comprise a plurality of active functional groups, i.e., groups that can chemically or physically modify a solution in contact with a surface of the hydrophilic polymer composition. Accordingly, in certain embodiments as otherwise described herein, one or more polysaccharides of the polymer component comprises a plurality of buffering functional groups. The person of ordinary skill in the art can select a number and type of buffering functional group to provide a desired buffering capacity and/or pH range. In certain such embodiments, the one or more polysaccharides having buffering functional groups are cross-linked (e.g., ionically cross-linked).

Also advantageously, the present inventors have determined that the one or more hydrophilic polymers (e.g., one or more polysaccharides) exposed on a hydrated surface of the composition can further be eluted into a solution in contact with the surface of the composition. Accordingly, in certain embodiments as otherwise described herein, one or more polysaccharides of the polymer component comprises a plurality of active functional groups that provide, for example, anti-inflammatory, antioxidant, antibacterial, or antifungal properties to a solution in contact with the surface of the composition. In certain embodiments as otherwise described herein, the polymer component further comprises an active component, such as, for example, a pharmaceutical compound, a protein, a peptide, a cell, or a mixture thereof. In certain such embodiments, the one or more polysaccharides (e.g., having active functional groups) are not cross-linked.

In certain embodiments as otherwise described herein, the polysaccharides, organic solvent, water, and active components are present in a combined amount of at least 80 wt. % of the polymer component. For example, in certain such embodiments, the polysaccharides, organic solvent, water, and active components are present in a combined amount of at least 85 wt. %, or at least 90 wt. %, or at least 92.5 wt. %, or at least 95 wt. %, or at least 97.5 wt. %, or at least 98 wt. %, or at least 99 wt. % of the polymer component.

In certain embodiments as otherwise described herein, the silicone component and the polymer component are present in a combined amount of at least 80 wt. % of the hydrophilic polymer composition. For example, in certain such embodiments, the silicone component and the polymer component are present in a combined amount of at least 85 wt. %, or at least 90 wt. %, or at least 92.5 wt. %, or at least 95 wt. %, or at least 97.5 wt. %, or at least 98 wt. %, or at least 99 wt. % of the hydrophilic polymer composition.

In certain embodiments as otherwise described herein, the silicone component and the polymer component are present in the hydrophilic composition in a dry weight ratio within the range of 95:5 to 40:60. For example, in certain such embodiments, the silicone component and the polymer component are present in the hydrophilic composition in a dry weight ratio within the range of 90:10 to 50:50, or 85:15 to 55:45, or 80:20 to 60:40, or 75:25 to 65:35. As used herein, dry weights exclude any liquids having a nominal boiling point at 1 atm of less than 150° C.

In certain embodiments as otherwise described herein, intimately mixing the silicone component and the polymer component comprises compounding in a roll mill. In other embodiments, intimately mixing the silicone component and the polymer component comprises compounding in a ross mixer. A variety of other means for mixing that provide sufficient shear to intimately mix the silicone component and the polymer component are known in the art.

In certain embodiments as otherwise described herein, the method for preparing a hydrophilic polymer composition further comprises forming the intimate mixture of the silicone component and the polymer component. The person of ordinary skill in the art will appreciate that the mixture may be formed into a variety of shapes such as, for example, tubes, sheets, etc. A variety of means for forming such shapes are known in the art, such as, for example, extrusion. The person of ordinary skill in the art will select extrusion conditions to provide desired extrudate properties (e.g., shape, size, etc.).

In certain embodiments as otherwise described herein, the method for preparing a hydrophilic polymer composition further comprises curing the intimate mixture (e.g., after forming the intimate mixture). In certain embodiments, curing provides cross-links between polysiloxanes. In certain embodiments, curing provides cross-links between polysiloxanes.

In certain embodiments as otherwise described herein, curing the intimate mixture comprises heating the mixture to a temperature within the range of 80° C. to 250° C. For example, in certain such embodiments, curing the curable article comprises heating the curable article to a temperature within the range of 80° C. to 225° C., or 80° C. to 200° C., or 80° C. to 175° C., or 80° C. to 150° C., or 90° C. to 250° C., or 100° C. to 250° C., or 125° C. to 250° C., or 150° C. to 250° C., or 90° C. to 200° C., or 100° C. to 160° C.

In certain embodiments as otherwise described herein, curing the intimate mixture comprises irradiating the mixture with actinic radiation. For example, in certain such embodiments, curing the intimate mixture comprises irradiating the mixture with radiation having a wavelength of less than 600 nm, such as, for example, radiation having a wavelength within the range of 200 nm to 300 nm, or 35 nm to 450 nm. In certain embodiments as otherwise described herein, the actinic radiation has an energy of at least about 20 mJ/cm$^2$, for example, at least about 30 mJ/cm$^2$, at least about 50 mJ/cm$^2$, or at least about 80 mJ/cm$^2$, or not greater than about 450 mJ/cm$^2$, for example, not greater than about 400 mJ/cm$^2$, not greater than about 350 mJ/cm$^2$, not greater than about 300 mJ/cm$^2$, not greater than about 250 mJ/cm$^2$, not greater than about 200 mJ/cm$^2$, or not greater than about 100 mJ/cm$^2$, or from about 20 mJ/cm$^2$ to about 450 mJ/cm$^2$, or from about 30 mJ/cm$^2$ to 300 mJ/cm$^2$, or from about 40 mJ/cm$^2$ to about 200 mJ/cm$^2$, or from about 20 mJ/cm$^2$ to about 100 mJ/cm$^2$.

For example, in certain embodiments as otherwise described herein, the mixture is cured at a UV power of at least 0.1 mW/cm$^2$, for example, at least 0.5 mW/cm$^2$, at least 1.0 mW/cm$^2$, or at least 3.0 mW/cm$^2$, or not greater than 250 mW/cm$^2$, for example, not greater than 150 mW/cm$^2$, or not greater than mW/cm$^2$, or not greater than 50 mW/cm$^2$, or not greater than 30 mW/cm$^2$, or not greater than 20 mW/cm$^2$, or not greater than 13.0 mW/cm$^2$, or not greater than 12 mW/cm$^2$, or not greater than 10 mW/cm$^2$.

Another aspect of the disclosure is a hydrophilic polymer composition made by a method as otherwise described herein. For example, in certain embodiments, the hydrophilic polymer composition is the product of curing an intimate mixture of a silicone component and a polymer component as otherwise described herein (e.g., by irradiating the intimate mixture with actinic radiation).

Another aspect of the disclosure is an article having a major exterior surface, the article comprising an intimate mixture of a silicone component including at least one polysiloxane, and a polymer component including at least one hydrophilic polymer having a water-absorption capacity of at least 50 wt. %. The silicone component and the polymer component are present in the composition in a dry weight ratio within the range of 99.9:1 to 30:70. In certain such embodiments, the article is the product of a method for preparing a hydrophobic polymer composition as otherwise described herein.

In certain embodiments as otherwise described herein, the silicone component comprises the cured product of a curable composition including one or more cross-linkable polysiloxane and an effective amount of a cross-linking agent as otherwise described herein.

For example, in certain such embodiments, the silicone component comprises the cured product of a curable composition including a first polysiloxane having at least about one silicon hydride group (e.g., at least about two silicon hydride groups), present in the curable composition in an amount within the range of 0.05 wt. % to 40 wt. % (e.g., 0.1 wt. % to 20 wt. %); a second polysiloxane having at least about one alkenyl group (e.g., at least about two alkenyl groups), present in the curable composition in an amount within the range of 2 wt. % to 99.95 wt. % (e.g., 20 wt. % to 99.9 wt. %); and an effective amount of a hydrosilylation catalyst, present in the silicone component, for example, in an amount within the range of 0.0001 wt. % to 1 wt. % (e.g., 0.0001 wt. % to 0.2 wt. %).

In another example, in certain such embodiments, the silicone component comprises the cured product of a curable composition including a first polysiloxane having at least about one silicon hydride group (e.g., at least about two silicon hydride groups), present in the silicone component in an amount within the range of 0.1 wt. % to 80 wt. % (e.g., 1 wt. % to 60 wt. %); a second polysiloxane having at least about one alkenyl group (e.g., at least about two alkenyl groups), present in the silicone component in an amount within the range of 2 wt. % to 99.9 wt. % (e.g., 20 wt. % to 99.9 wt. %); and an effective amount of a hydrosilylation catalyst, present in the silicone component, for example, in an amount within the range of 0.0001 wt. % to 1 wt. % (e.g., 0.0001 wt. % to 0.2 wt. %).

In certain such embodiments, the hydrosilylation catalyst is present in the curable composition in an effective amount, for example, within the range of 0.0001 wt. % to 1 wt. %.

In certain such embodiments, one or more polysiloxanes of the curable composition comprises at least about one reactive heterocycloalkyl group. The present inventors have determined that, advantageously, the cured product of the curable composition can include cross-links between polysiloxanes of the silicone component and one or more hydrophilic polymers (e.g., one or more polysaccharides) of the polymer component. Accordingly, in certain embodiments as otherwise described herein, one or more polysiloxanes of the silicone component is covalently bonded to a hydrophilic polymer (e.g., a polysaccharide) of the polymer component.

In certain embodiments, the silicone component of the article further comprises one or more particulate fillers as otherwise described herein. For example, in certain such embodiments, the silicone component further comprises a filler selected from ceramic particles, glass particles, metallic particles, polymeric particles, or any combination thereof. In certain such embodiments, the filler is present in the silicone component in an amount within the range of 1 wt. % to 70 wt. % (e.g., 10 wt. % to 40 wt. %, or 30 wt. % to 60 wt. %). In certain embodiments as otherwise described herein, the filler comprises silica, titania, or a mixture thereof.

In certain embodiments, the silicone component of the article further comprises one or more inhibitors as otherwise described herein. For example, in certain such embodiments, one or more inhibitors is present in the silicone component in an amount within the range of 0.002 wt. % to 1 wt. % (e.g., 0.002 wt. % to 0.2 wt. %, or 0.005 wt. % to 0.05 wt. %).

In certain embodiments as otherwise described herein, the polysiloxanes, cross-linking agents, fillers, and inhibitors are present in a combined amount of at least 80 wt. % of the silicone component of the article. For example, in certain such embodiments, the polysiloxanes, cross-linking agents, fillers, and inhibitors are present in a combined amount of at least 90 wt. %, at least 95 wt. %, or at least 97.5 wt. % of the silicone component of the article.

In certain embodiments, the polymer component of the article comprises a hydrophilic polymer having a water-absorption capacity as otherwise described herein. For example, in certain such embodiments, the polymer component comprises a hydrophilic polymer having a water-absorption capacity of at least 75 wt. %, or at least 100 wt. %.

For example, in certain such embodiments, the polymer component comprises a polyvinyl alcohol. In another example, in certain such embodiments, the polymer component comprises a polyvinyl pyrrolidone.

In certain embodiments, the polymer component of the article comprises one or more saccharides (e.g., oligosaccharides and/or polysaccharides) as otherwise described herein.

The present inventors have determined that the exterior surface of an article having a polymer component comprising one or more ionic polysaccharides can advantageously have anti-fungal or anti-bacterial properties. Accordingly, in certain embodiments as otherwise described herein, the polymer component of the article comprises one or more ionic polysaccharides.

In another example, the polymer component comprises one or more polysaccharides selected from starch, alginate, cellulose, hyaluronic acid, chitin, and derivatives thereof. In certain such embodiments, the polymer component comprises cellulose or a cellulose derivative (e.g., carboxymethyl cellulose). In certain such embodiments, the polymer component comprises alginate. In certain such embodiments, the polymer component comprises hyaluronic acid. In certain such embodiments, the polymer component comprises starch.

In certain embodiments, the polymer component of the article comprises a polysaccharide comprising 1,4-α-linked repeat units according to Formula I as otherwise described herein. In certain embodiments, the polymer component of the article comprises a polysaccharide comprising 1,4β-linked repeat units according to Formulas II and III as otherwise described herein. In certain embodiments, the polymer component of the article comprises a polysaccharide comprising 1,4β-linked repeat units according to Formula IV as otherwise described herein. In certain embodiments, the polymer component of the article comprises a polysaccharide comprising 1,4β-linked repeat units repeat units according to Formula V as otherwise described herein.

In certain embodiments, the polymer component of the article comprises one or more ionically cross-linked polysaccharides (e.g., a $Ca^{2+}$-cross-linked polysaccharide) such as, for example, a $Ca^{2+}$-cross-linked carboxymethyl cellulose. In certain embodiments, the polymer component of the article comprises one or more covalently cross-linked polysaccharides.

Advantageously, the present inventors have determined that a hydrophilic polymer (e.g., an oligo- or polysaccharide) lacking siloxane functionality can be intimately mixed (e.g., according to a method as otherwise described herein) with a silicone component to provide an article with an exterior surface having desirable optical and mechanical properties. Of course, in other embodiments, the article can include a hydrophilic polymer comprising a siloxane group.

In certain embodiments, the intimate mixture of the article further comprises a liquid as otherwise described herein, i.e., having a cellulose-swelling capacity of at least 20 wt. %. For example, in certain such embodiments, the liquid comprises (e.g., is) a polar solvent selected from methanol, ethanol, acetone, or acetonitrile. In another example, the liquid comprises (e.g., is) water.

In certain embodiments as otherwise described herein, the weight ratio of the combined amount of hydrophilic polymers (i.e., the one or more hydrophilic polymers comprising the polymer component) to water is within the range of 10:90 to 95:5. For example, in certain such embodiments, the weight ratio of the combined amount of hydrophilic polymers to water is within the range of 20:80 to 95:5, or 30:70 to 95:5, or 40:60 to 95:5, or 50:50 to 95:5, or 60:40 to 95:5, or 70:30 to 95:5, or 10:90 to 90:10, or 10:90 to 80:20, or 10:90 to 70:30, or 10:90 to 60:40, or 10:90 to 50:50, or 10:90 to 40:60, or 10:90 to 30:70, or 20:80 to 80:20, or 30:70 to 70:30.

Advantageously, the present inventors have determined that the water and one or more hydrophilic polymers (e.g., one or more polysaccharides) of the intimate mixture (e.g., prepared according to a method as otherwise described herein) can form a hydrogel. Accordingly, in certain embodiments, the exterior surface of the article comprises a hydrogel formed from water and one or more hydrophilic polymers as otherwise described herein (e.g., one or more polysaccharides).

The present inventors have further determined that the exterior surface of an article comprising one or more hydrophilic polymers (e.g., one or more polysaccharides) comprising a plurality of buffering functional groups can, advantageously, buffer the pH of an aqueous solution in contact with the exterior surface. Accordingly, in certain embodiments, one or more hydrophilic polymers of the polymer component comprises a plurality of buffering groups. The person of ordinary skill in the art can select a number and type of buffering functional groups to provide a desired buffering capacity and/or pH range. For example, in certain such embodiments, the article is capable of maintaining the pH of an aqueous solution in contact with the exterior surface within the range of 5 to 9.

Also advantageously, the present inventors have determined that one or more active components comprising an article as otherwise described herein can be eluted into a solution in contact with the exterior surface. Accordingly, in certain embodiments, the exterior surface of the article comprises one or more active components as otherwise described herein. In certain such embodiments, the one or more active components are selected pharmaceutical compounds, proteins, peptides, cells, or any mixture thereof. Of course, the active component may in certain embodiments be distributed relatively evenly throughout the article (e.g., included in the intimate mixture), or in other embodiments may be localized in the exterior surface (e.g., deposited onto the exterior surface). In certain embodiments, the active component is distributed throughout the article, and the active component content of the exterior surface can be renewed, for example, as the active component is eluted into a solution in contact with the exterior surface.

Similarly, the present inventors have determined that one or more hydrophilic polymers (e.g., polysaccharides) comprising an article as otherwise described herein can be eluted into a solution in contact with the exterior surface. In certain embodiments, the hydrophilic polymer content of the exterior surface can be renewed, for example, as the hydrophilic polymer is eluted into a solution in contact with the exterior surface.

Accordingly, in certain embodiments, the article as otherwise described herein is capable of releasing one or more active components into an aqueous solution in contact with the exterior surface at a rate of at least 1 milligram (e.g., 2 mg, or 3 mg, or 4 mg, or 5 mg) of active component per hour, per square centimeter of exterior surface.

In certain embodiments, the article as otherwise described herein is capable of releasing one or more hydrophilic polymers (e.g., one or more polysaccharides) into an aqueous solution in contact with the exterior surface at a rate of at least 1 milligram (e.g., 2 mg, or 3 mg, or 4 mg, or 5 mg) of active component per hour, per square centimeter of exterior surface. Of course, in other embodiments, one or more (e.g., all) of the hydrophilic polymers of the polymer are not releasable (e.g., into an aqueous solution in contact with the exterior surface).

The present inventors have also determined that the exterior surface of an article as otherwise described herein (e.g., prepared according to a method as otherwise described herein) can have an advantageously low coefficient of friction. For example, in certain embodiments as otherwise described herein, the coefficient of friction of the exterior surface is less than 0.1, or less than 0.075, or less than 0.05, or less than 0.03.

The present inventors have determined that hydrophilic materials as described herein can be made with a variety of contact angles. Contact angles are measured by goniometry with water at 23° C. at 50% relative humidity, measured after the droplet being disposed on the surface for ten seconds. In certain embodiments, articles as described herein have a contact angle no more than 80 degrees, e.g., no more than 65 degrees or no more than 50 degrees. For example, in certain embodiments as otherwise described herein, an article as described herein has a contact angle in the range of 10-80 degrees, e.g., 10-65 degrees, or 10-50 degrees, or 20-80 degrees, or 20-65 degrees, or 20-50 degrees, or 40-80 degrees, or 40-65 degrees. This in contrast with conventional silicones, which tend to have much higher contact angles. Moreover, the hydrophilicity of the materials is especially stable, with contact angles changing no more than 5 degrees over 6 months storage at 50% relative humidity at 23° C.

In certain embodiments, the exterior surface of an article as otherwise described herein (e.g., prepared according to a method as otherwise described herein) has a light transmissivity of at least 25%, for example, for light having a wavelength within the range of 400 nm to 700 nm. For example, in certain such embodiments, the transmissivity of the exterior surface is at least 30%, or at least 35% for light having a wavelength within the range of 400 nm to 700 nm.

In certain embodiments, the entirety of an article can be formed of the intimate mixture. However, in other especially desirable embodiments, the intimate mixture can be provided as a surface layer of an article, with the bulk of the article being formed of other material(s). Thus, in certain embodiments, the intimate mixture is formed as a layer on a substrate, with the substrate being another material of the article, e.g., a silicone material. The person of ordinary skill in the art will appreciate that a variety of methods can be used to form surface layers of the intimate mixtures described herein, including conventional reactive coextrusion and coating methods.

Figure 2:
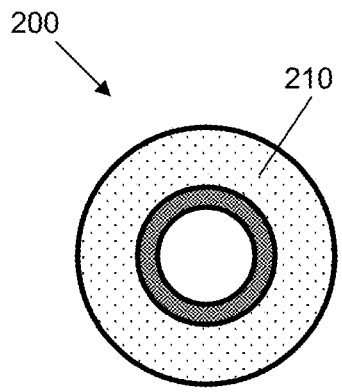
FIG. 2 is a cross-sectional schematic view of an article according to another embodiment of the disclosure.

In certain embodiments, an article as otherwise described herein (e.g., prepared according to a method as otherwise described herein) is in the form of a tubular article, such as catheter. A cross-sectional view of a catheter is shown in FIG. 1. Here, catheter 100 has an outer layer 105 formed on a substrate layer 110. The inner layer 105 can be formed of an intimate mixture as described herein. In certain such embodiments, the coefficient of friction of the exterior surface of the tubular article (e.g., catheter) is less than 0.1, or less than 0.05. In certain embodiments, an article as otherwise described herein (e.g., prepared according to a method as otherwise described herein) is in the form of a beverage tube. In certain such embodiments, one or more hydrophilic polymers of the beverage tube comprise a plurality of buffering functional groups. An example is shown in cross-sectional view in FIG. 2. Here, the beverage tube 200 has an inner layer 215 disposed on a substrate 210, with the inner layer formed of an intimate mixture as described herein.

In certain embodiments, an article as otherwise described herein (e.g., prepared according to a method as otherwise described herein) is in the form of a wound dressing. In certain such embodiments, the coefficient of friction of the exterior surface of the wound dressing is less than 0.1, or less than 0.05. In certain such embodiments, the exterior surface of the wound dressing comprises one or more active components (e.g., a pharmaceutical compound) that can be eluted into an aqueous solution in contact with the exterior surface. In certain such embodiments, one or more hydrophilic polymers of the wound dressing (e.g., one or more polysaccharides) can be eluted into an aqueous solution in contact with the exterior surface. The wound dressing can be formed, e.g., as a substantially planar sheet of material, with a surface layer of intimate mixture as described above, or alternatively as a sheet of the intimate mixture itself.

EXAMPLES

The Examples that follow are illustrative of specific embodiments of the invention, and various uses thereof. They are set forth for explanatory purposes only, and are not to be taken as limiting the invention.

Example 1. Composition Preparation

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 1 having a dry-weight ratio of silicone to carboxymethyl cellulose of 95:5.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 2 having a dry-weight ratio of silicone to carboxymethyl cellulose of 90:10.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 3 having a dry-weight ratio of silicone to carboxymethyl cellulose of 80:20.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component including an epoxide-functionalized polysiloxane via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 4 having a dry-weight ratio of silicone to carboxymethyl cellulose of 80:20 and including 2 wt. % of the epoxide-functionalized polysiloxane.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP), water, and chitosan was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 5 having a dry-weight ratio of silicone to carboxymethyl cellulose to chitosan of 75:20:5.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 6 having a dry-weight ratio of silicone to carboxymethyl cellulose of 50:50.

A slurry including deionized water and alginate was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. The compounded material was then molded in a heat-pressure press for 15 min. at 205° F., at about 20 ton, to provide composition 7 having a dry-weight ratio of silicone to alginate of 65:35.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (high-consistency rubber base; 1:1 40 duro:60 duro) via rubber mill. The mixture was milled for at least 20 passes, until the compounded material appeared homogenous. An inhibitor was added to the mill, and then a cross-linking catalyst was added to the mill. Then, $CaCl_2$) was added to the mill. The compounded material was molded in a heat-pressure press for 15 min. at 205° F., at about 20 ton, to provide composition 8 having a dry-weight ratio of silicone to $Ca^{2+}$-cross-linked carboxymethyl cellulose of 80:20.

A slurry including high-viscosity fine-mesh sodium carboxymethylcellulose (minimum molar mass 17,000; hot- and cold-water soluble, stable over pH 4.0-10.0; viscosity (1%, LV@30 rpm, 25° C.) 4,000-7,000 cP) and deionized water was slowly added to a silicone component (UV liquid silicone rubber base) in a Ross mixer. A photoactive cross-linking catalyst was then added to the mixer. The mixture was blended at 30 rpm for at least 20 minutes, until the compounded material appeared homogenous. The compounded material was irradiated with 254-nm radiation (15 mW/cm²) for 6 minutes to provide composition 9.

Example 2. Mass Extraction

A first set of samples of compositions 1-7 of Example 1 were weighed immediately after molding to provide a mass $m_1$. The samples were then dried under vacuum (80° C.; 1 bar) for 24 hours and then weighed again to provide a mass $m_2$. A second set of samples of compositions 1-7 were weighed immediately after molding to provide a mass $m_0$, and then were placed in deionized water for 24 hours. The swelled samples were weighed to provide a mass $m_3$. The "swelling ratio" of each sample was calculated according to Formula I:

$$m_3/(m_0 \times (m_2/m_1)) \times 100\% \quad (I)$$

and the "loss after extraction" of each sample was calculated according to Formula II:

$$(m_0 \times (m_2/m_1) - m_4)/(m_0 \times (m_2/m_1)) \times 100\% \quad (II)$$

The results for samples 1-7, as well as for a comparative sample (100% silicone, sample C) are provided in Table 1, below. Notably, the results of Example 2 demonstrate that the elution of one or more hydrophilic polymers of the composition can be avoided, or if desired, adjusted to a certain rate of elution.

TABLE 1

Mass Extraction Data

| Sample | Swelling Ratio (%) | Loss After Extraction (wt. %) |
|---|---|---|
| C | 1.5 ± 0.1 | 0.12 ± 0.01 |
| 1 | 9.5 ± 0.3 | 0.2 ± 0.2 |
| 2 | 21.1 ± 0.7 | 1.1 ± 0.2 |
| 3 | 165.4 ± 16.5 | 4.6 ± 0.6 |
| 4 | 60.0 ± 5.7 | 3.2 ± 0.1 |
| 5 | 225.8 ± 0.25 | 1.7 ± 0.3 |
| 6 | 1805.5 ± 42.0 | 30.5 ± 3.7 |
| 7 | 38.8 ± 0.9 | 2.5 ± 0.5 |

Example 3. Light Transmission

Figure 3:
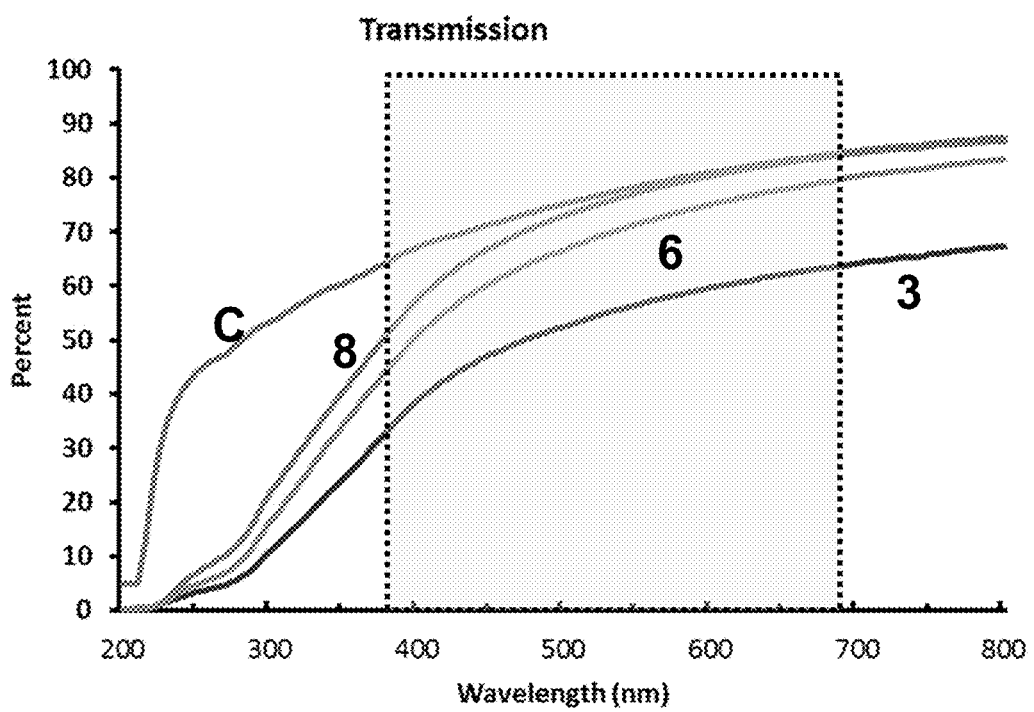
FIG. 3 is a plot of the UV-visible light transmissivity of certain compositions described herein.

The light transmissivity of samples of compositions 3, 6, and 8, as well as comparative composition C, was measured with a UV-vis spectrophotometer. The results, shown in FIG. 3, show that the light transmissivity of the compositions was greater than 30% for light having a wavelength of 400-700. Notably, the results of Example 3 indicate that each of the samples has a desirable optical transparency across the visible-light spectrum.

Example 4. Hydrophilicity

Figure 4:
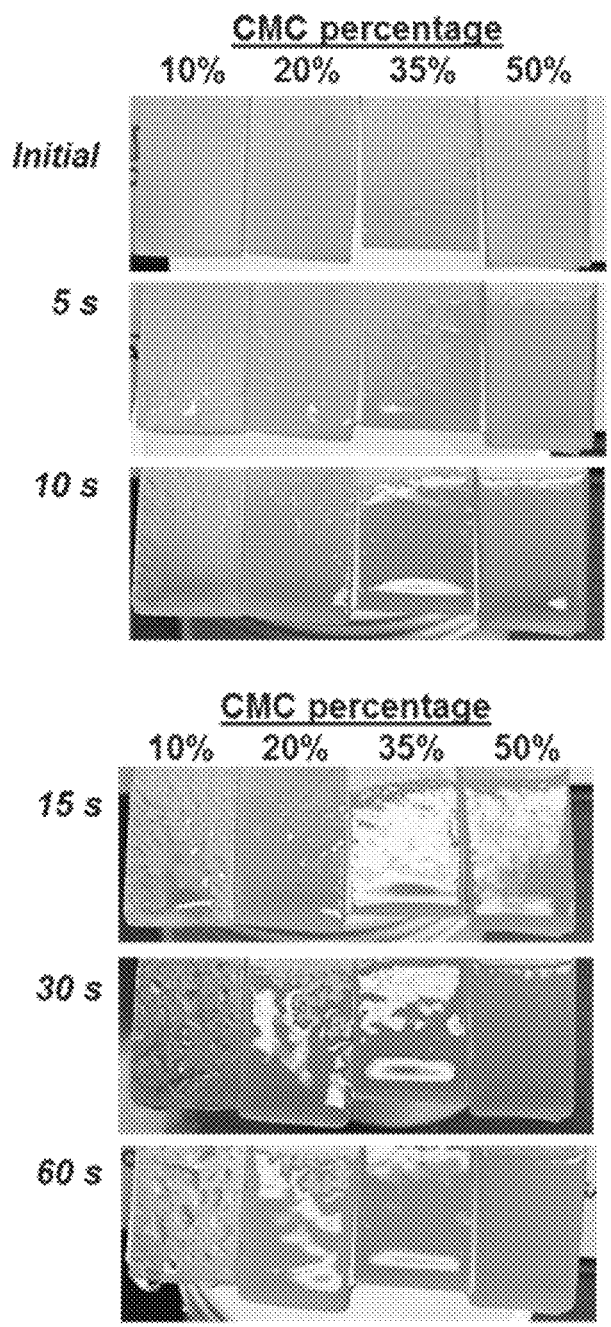
FIG. 4 is an image of test samples after being submerged in water.

As test of hydrophilicity, samples made generally as described above, with different percents by weight of carboxymethyl cellulose were submerged in a beaker of water at room temperature. Samples were removed at a number of times throughout the experiment; at each such time, an image was acquired and the sample replaced in the water. Images at various soak times for various wt % values of carboxymethylcellulose are provided in FIG. 4. The beading of the water demonstrates that materials with more carboxymethylcellulose were more hydrophilic.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Numerous references have been made to patents and printed publications throughout this specification. Each of the cited references and printed publications are individually incorporated herein by reference in their entirety.

Furthermore, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH2$-$CH2$-), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)a, wherein a is 0 or 1. In such instances, when a is 0 the moiety is —B and when a is 1 the moiety is —B-A.

As used herein, the term "hydrocarbon" includes linear hydrocarbons, branched hydrocarbons, acyclic hydrocarbons, alicyclic hydrocarbons, and aromatic hydrocarbons, including, for example, alkyl, alkoxy, alkenyl, alkynyl, aryl, heteroaryl, heterocycloalkyl, and cycloalkyl.

As used herein, the term "alkyl" includes a saturated hydrocarbon having a designed number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6. Alkyl group may be straight or branched and depending on context, may be a monovalent radical or a divalent radical (i.e., an alkylene group). For example, the moiety "—($C_1$-$C_6$ alkyl)-O—" signifies connection of an oxygen through an alkylene bridge having from 1 to 6 carbons and $C_1$-$C_3$ alkyl represents methyl, ethyl, and propyl moieties. Examples of "alkyl" include, for example, methyl, ethyl, propyl, isopropyl, butyl, iso-, sec-, and tert-butyl, pentyl, and hexyl.

The term "alkoxy" represents an alkyl group of an indicated number of carbon atoms attached to the parent molecular moiety through an oxygen bridge. Examples of "alkoxy" include, for example, methoxy, ethoxy, propoxy, and isopropoxy.

As used herein, the term "alkenyl" includes unsaturated hydrocarbons containing from 2 to 10 carbons (i.e., inclusive of 2 and 10), 2 to 8 carbons, 2 to 6 carbons, or 2, 3, 4, 5, or 6, unless otherwise specified, and containing at least one carbon-carbon double bond. An alkenyl group may be straight or branched and depending on context, may be a monovalent radical or a divalent radical (i.e., an alkenylene group). For example, the moiety "—(C$_2$-C$_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

As used herein, the term "alkynyl" includes unsaturated hydrocarbons containing from 2 to 10 carbons (i.e., inclusive of 2 and 10), 2 to 8 carbons, 2 to 6 carbons, or 2, 3, 4, 5, or 6, unless otherwise specified, and containing at least one carbon-carbon triple bond. An alkynyl group may be straight or branched and depending on context, may be a monovalent radical or a divalent radical (i.e., an alkynylene group). For example, the moiety "—(C$_2$-C$_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocycle rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can, unless stated otherwise, be substituted in one or more substitutable positions with various groups, as indicated.

The terms "halogen" or "halo" indicate fluorine, chlorine, bromine, and iodine.

The term "heteroaryl" refers to an aromatic ring system containing at least one heteroatom selected from nitrogen, oxygen and sulfur. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted," can, unless stated otherwise, be substituted in one or more substitutable positions with various groups, as indicated.

The term "heterocycloalkyl" refers to a non-aromatic ring or ring system containing at least one heteroatom that is selected from nitrogen, oxygen and sulfur, wherein said heteroatom is in a non-aromatic ring. The heterocycloalkyl may have 1, 2, 3, or 4 heteroatoms. The heterocycloalkyl may be saturated (i.e., a heterocycloalkyl) or partially unsaturated (i.e., a heterocycloalkenyl). Heterocycloalkyl includes monocyclic groups of 3 to 8 annular atoms as well as bicyclic and polycyclic ring systems, including bridged and fused systems, wherein each ring includes 3 to 8 annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6, or 7 members in a single ring. Examples of heterocycloalkyl groups include, for example, azabicyclo[2.2.2]octyl, azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted," can, unless stated otherwise, be substituted in one or more substitutable positions with various groups, as indicated.

Specifically, "reactive heterocycloalkyl" refer to heterocycloalkyl groups that are reactive to functional groups of a hydrophilic polymer as otherwise described herein (e.g., an alcohol group of a polysaccharide). Reactive heterocycloalkyl groups include cyclic ethers such as, for example, epoxides and oxetanes, and cyclic thioethers, such as episulfide groups. In certain embodiments as disclosed herein, "reactive heterocycloalkyl" refers herein to epoxide groups.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally may be fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6, or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted," may be substituted in one or more substitutable positions with various groups, as indicated.

The term "siloxane" refers generally to materials including the linkage Si—O—Si. The term "siloxane" may refer to disiloxane, i.e., R3Si—O—Si—R3, or polysiloxane, i.e., R3Si—O—[SiR2—O]n-SiR3, wherein n is at least one. As used herein, the term "siloxane" includes cyclic polysiloxanes. The term "siloxane repeat unit" or "siloxane group" refers to the repeating —[SiR2-O]— units comprising a polysiloxane. For example, hexamethyldisiloxane is a siloxane, and poly(dimethylsiloxane) and methyl hydrosiloxane-dimethylsiloxane copolymer are polysiloxanes.

The term "silane" refers to saturated chemical compounds consisting of one or multiple silicon atoms linked to each other or one or multiple atoms of other chemical elements as the centers of multiple single bonds. For example, tetrakis (dimethylsilyl) orthosilicate and tetramethyl silane are silanes. The person of ordinary skill in the art will appreciate that certain siloxanes, e.g., tetrakis(dimethylsilyl) orthosilicate, may also be referred to as silanes.

The term "hydride" refers to a hydrogen group bonded to a more electropositive element or group. For example, calcium hydride and sodium hydride both comprise hydride groups. In another example, trimethylsilane and hydride-terminated poly(dimethylsiloxane) both comprise hydride groups.

The term "substituted," when used to modify a specified group or radical, means that one or more hydrogen atoms of the specified group or radical are each, independently of one another, replaced with the same or different substituent groups as defined below, unless specified otherwise.

The terms "polymerizable" and "polymerized" refer to one or more compounds that can be reacted to provide a larger compound, and to one or more compounds that have been reacted to provide a larger compound, respectively. For example, a composition of a single compound may be polymerizable (i.e., a monomer), and, upon polymerization, may provide a polymerized compound comprising repeating monomer units. Polymerizable or polymerized compositions may also include "curable" or "cured" compositions, or "cross-linkable" or "cross-linked" compositions, in which compositions comprising polymers and, optionally, monomers and/or cross-linkers, can be, or have been, reacted to provide a composition of larger compounds.

Additional aspects of the disclosure are provided by the following enumerated embodiments, which can be combined in any number and in any fashion not technically or logically inconsistent.

Embodiment 1

An article having a major exterior surface, the article comprising an intimate mixture of
  a silicone component including at least one polysiloxane; and
  a polymer component including at least one hydrophilic polymer having a water-absorption capacity of at least 50 wt. %;
wherein the silicone component and the polymer component are present in the mixture in a dry weight ratio within the range of 99.9:0.1 to 30:70.

Embodiment 2

The article of embodiment 1, wherein the intimate mixture is at disposed an exterior surface of the article.

Embodiment 3

The article of embodiment 2, wherein the intimate mixture is disposed at the major exterior surface of the article.

Embodiment 4

The article of any of embodiments 1-3, wherein the silicone component comprises the cured product of a curable composition including one or more cross-linkable polysiloxanes and an effective amount of a cross-linking agent.

Embodiment 5

The article of embodiment 4, wherein the curable composition includes
  a first polysiloxane having at least about one silicon hydride group (e.g., at least about two silicon hydride groups), present in the curable composition in an amount within the range of 0.05 wt. % to 40 wt. % (e.g., 0.1 wt. % to 20 wt. %);
  a second polysiloxane having at least about one alkenyl group (e.g., at least about two alkenyl groups), present in the curable composition in an amount within the range of 2 wt. % to 99.95 wt. % (e.g., 20 wt. % to 99.9 wt. %); and
  an effective amount of a hydrosilylation catalyst, present in the silicone component, for example, in an amount within the range of 0.0001 wt. % to 1 wt. % (e.g., 0.0001 wt. % to 0.2 wt. %).

Embodiment 6

The article of embodiment 4, wherein the curable composition includes
  a first polysiloxane having at least about one silicon hydride group (e.g., at least about two silicon hydride groups), present in the silicone component in an amount within the range of 0.1 wt. % to 80 wt. % (e.g., 1 wt. % to 60 wt. %);
  a second polysiloxane having at least about one alkenyl group (e.g., at least about two alkenyl groups), present in the silicone component in an amount within the range of 2 wt. % to 99.9 wt. % (e.g., 20 wt. % to 99.9 wt. %); and an effective amount of a hydrosilylation catalyst, present in the silicone component, for example, in an amount within the range of 0.0001 wt. % to 1 wt. % (e.g., 0.0001 wt. % to 0.2 wt. %).

Embodiment 7

The article of any of embodiments 4-6, wherein one or more polysiloxanes of the curable composition comprises at least about one reactive heterocycloalkyl group.

Embodiment 8

The article of any of embodiments 1-7, wherein the silicone component further comprises a filler selected from ceramic particles, glass particles, metallic particles, polymeric particles, or any combination thereof, present in the silicone component in an amount within the range of 1 wt. % to 70 wt. %.

Embodiment 9

The article of embodiment 8, wherein the filler comprises silica, titania, or a mixture thereof.

Embodiment 10

The article of any of embodiments 1-9, wherein the silicone component comprises one or more inhibitors, present in the silicone component in an amount within the range of 0.002 wt. % to 1 wt. % (e.g., 0.002 wt. % to 0.2 wt. %, or 0.005 wt. % to 0.05 wt. %).

Embodiment 11

The article of any of embodiments 1-10, wherein the polysiloxanes, cross-linking agents, fillers, and inhibitors are present in a combined amount of at least 80 wt. % (e.g., at least 90 wt. %, or at least 97.5 wt. %) of the silicone component.

Embodiment 12

The article of any of embodiments 1-11, wherein the polymer component comprises a hydrophilic polymer having a water-absorption capacity of at least 75 wt. % (e.g., at least 100 wt. %).

Embodiment 13

The article of any of embodiments 1-12, wherein the polymer component comprises a polyvinyl alcohol.

Embodiment 14

The article of any of embodiments 1-12, wherein the polymer component comprises a polyvinyl pyrrolidone.

Embodiment 15

The article of any of embodiments 1-13, wherein the polymer component comprises one or more saccharides (e.g., one or more oligosaccharides and/or polysaccharides).

Embodiment 16

The article of embodiment 15, wherein the polymer component comprises one or more ionic polysaccharides.

Embodiment 17

The article of embodiment 15, wherein the polymer component comprises one or more polysaccharides selected from starch, alginate, cellulose, hyaluronic acid, chitin, and derivatives thereof.

Embodiment 18

The article of any of embodiments 15-17, wherein the polymer component comprises one or more ionically cross-linked polysaccharides (e.g., a $Ca^{2+}$-cross-linked polysaccharide).

Embodiment 19

The article of any of embodiments 1-18, wherein none of the hydrophilic polymers of the polymer component comprise a siloxane group.

Embodiment 20

The article of any of embodiments 1-19, wherein one or more polysiloxanes of the silicone component is cross-linked via covalent bonding to a hydrophilic polymer of the polymer component.

Embodiment 21

The article of any of embodiments 1-20, wherein the intimate mixture further comprises a liquid having a cellulose-swelling capacity of at least 20 wt. %.

Embodiment 22

The article of any of embodiments 1-21, wherein the intimate mixture further comprises a polar organic solvent selected from methanol, ethanol, acetone, or acetonitrile.

Embodiment 23

The article of any of embodiments 1-22, wherein the intimate mixture further comprises water.

Embodiment 24

The article of embodiment 23, wherein the weight ratio of the combined amount of hydrophilic polymers to water in the intimate mixture is within the range of 10:90 to 95:5.

Embodiment 25

The article of embodiment 23, wherein the weight ratio of the combined amount of hydrophilic polymers to water in the intimate mixture is within the range of 30:70 to 70:30.

Embodiment 26

The article of any of embodiments 23-25, wherein the exterior surface comprises a hydrogel formed from the water and the one or more hydrophilic polymers.

Embodiment 27

The article of any of embodiments 1-26, wherein the silicone component and the polymer component are present in the composition in a dry weight ratio within the range of 95:5 to 40:60 (e.g., 90:10 to 50:50, or 85:15 to 55:45)

Embodiment 28

The article of any of embodiments 1-27, wherein one or more hydrophilic polymers of the polymer component comprises a plurality of buffering functional groups.

Embodiment 29

The article of embodiment 28, capable of maintaining the pH of an aqueous solution in contact with the exterior surface within the range of 5 to 9.

Embodiment 30

The article of any of embodiments 1-29, wherein the exterior surface further comprises one or more active components.

Embodiment 31

The article of embodiment 30, wherein the one or more active components are selected from pharmaceutical compounds, proteins, peptides, cells, or a mixture thereof.

Embodiment 32

The article of embodiment 30 or 31, capable of releasing the one or more active components into an aqueous solution in contact with the exterior surface at a rate of at least 1 milligram of active component per hour, per square centimeter of exterior surface.

Embodiment 33

The article of any of embodiments 1-32, capable of releasing one or more hydrophilic polymers into an aqueous solution in contact with the exterior surface at a rate of at least 1 milligram of hydrophilic polymer per hour, per square centimeter of exterior surface.

Embodiment 34

The article of any of embodiments 1-32, where one or more hydrophilic polymers cannot be released into an aqueous solution in contact with the exterior surface.

Embodiment 35

The article of any of embodiments 1-34, wherein the coefficient of friction of the exterior surface is less than 0.1 (e.g., less than 0.075, less than 0.05, or less than 0.03)

Embodiment 36

The article of any of embodiments 1-35, wherein the transmissivity of the major exterior surface is at least 25% (e.g., at least 30%, or at least 35%) for light having a wavelength within the range of 400 nm to 700 nm.

Embodiment 37

The article of any of embodiments 1-36, wherein the major exterior surface has a contact angle of no more than 80 degrees, e.g., no more than 65 degrees, or no more than 50 degrees.

Embodiment 38

The article of any of embodiments 1-36, wherein the major exterior surface has a contact angle in the range of 10-80 degrees, e.g., 10-65 degrees, or 10-50 degrees, or 20-80 degrees, or 20-65 degrees, or 20-50 degrees, or 40-80 degrees, or 40-65 degrees.

Embodiment 39

The article of claim 37 or claim 38, wherein the contact angle does not change more than 5 degrees over 6 months storage at 50% relative humidity and 23° C.

Embodiment 40

The article of any of embodiments 1-39, wherein the intimate mixture is formed as a layer on a substrate.

Embodiment 41

The article of any of embodiments 1-40, in the form of a tubular article.

Embodiment 42

The article of any of embodiments 1-40, in the form of a catheter or a beverage tube.

Embodiment 43

The article of any of embodiments 1-40, in the form of a wound dressing.

Embodiment 44

A method for preparing a hydrophilic polymer composition, the method comprising intimately mixing
a silicone component including at least one polysiloxane; and
a polymer component including at least one hydrophilic polymer having a water-absorption capacity of at least 50 wt. %;
wherein the silicone component and the polymer component are present in the composition in a dry weight ratio within the range of 99.9:0.1 to 30:70.

Embodiment 45

The method of embodiment 44, wherein the silicone component comprises
a cross-linkable polysiloxane, present in the silicone component in an amount within the range of 2 wt. % to 99.9 wt. % (e.g., 30 wt. % to 99.9 wt. %); and
an effective amount of a cross-linking agent.

Embodiment 46

The method of embodiment 45, wherein the cross-linkable polysiloxane comprises one or more groups selected from alkenyl groups and silicon hydride groups, and the cross-linking agent comprises a thermally active initiator selected from di-aralkyl peroxides, alkyl-aralkyl peroxides, and di-alkyl peroxides.

Embodiment 47

The method of embodiment 44, wherein the silicone component comprises
- a first polysiloxane having at least about one silicon hydride group (e.g., at least about two silicon hydride groups), present in the silicone component in an amount within the range of 0.05 wt. % to 40 wt. % (e.g., 0.1 wt. % to 20 wt. %);
- a second polysiloxane having at least about one alkenyl group (e.g., at least about two alkenyl groups), present in the silicone component in an amount within the range of 2 wt. % to 99.95 wt. % (e.g., 20 wt. % to 99.9 wt. %); and
- an effective amount of a hydrosilylation catalyst, present in the silicone component, for example, in an amount within the range of 0.0001 wt. % to 1 wt. % (e.g., 0.0001 wt. % to 0.2 wt. %).

Embodiment 48

The method of embodiment 44, wherein the silicone component comprises
- a first polysiloxane having at least about one silicon hydride group (e.g., at least about two silicon hydride groups), present in the silicone component in an amount within the range of 0.1 wt. % to 80 wt. % (e.g., 1 wt. % to 60 wt. %);
- a second polysiloxane having at least about one alkenyl group (e.g., at least about two alkenyl groups), present in the silicone component in an amount within the range of 2 wt. % to 99.9 wt. % (e.g., 20 wt. % to 99.9 wt. %); and
- an effective amount of a hydrosilylation catalyst, present in the silicone component, for example, in an amount within the range of 0.0001 wt. % to 1 wt. % (e.g., 0.0001 wt. % to 0.2 wt. %).

Embodiment 49

The method of embodiment 47 or 48, wherein the hydrosilylation catalyst is a photoactive catalyst (e.g., a photoactive platinum catalyst).

Embodiment 50

The method of embodiment 47 or 48, wherein the hydrosilylation catalyst is a thermally active catalyst (e.g., a thermally active platinum catalyst).

Embodiment 51

The method of any of embodiments 44-50, wherein one or more polysiloxanes of the silicone component comprises at least about one reactive heterocycloalkyl group.

Embodiment 52

The method of any of embodiments 44-51, wherein the silicone component comprises one or more inhibitors, present in the silicone component in an amount within the range of 0.002 wt. % to 1 wt. % (e.g., 0.002 wt. % to 0.2 wt. %, or 0.005 wt. % to 0.05 wt. %).

Embodiment 53

The method of any of embodiments 44-52, wherein the silicone component further comprises a filler selected from ceramic particles, glass particles, metallic particles, polymeric particles, or any combination thereof, present in the silicone component in an amount within the range of 1 wt. % to 70 wt. %.

Embodiment 54

The method of embodiment 53, wherein the filler comprises silica, titania, or a mixture thereof.

Embodiment 55

The method of any of embodiments 44-54, wherein the polysiloxanes, cross-linking agents, fillers, and inhibitors are present in a combined amount of at least 80 wt. % (e.g., at least 90 wt. %, or at least 97.5 wt. %) of the silicone component.

Embodiment 56

The method of any of embodiments 44-55, wherein the polymer component comprises a hydrophilic polymer having a water-absorption capacity of at least 75 wt. % (e.g., at least 100 wt. %).

Embodiment 57

The method of any of embodiments 44-56, wherein the at least one hydrophilic polymer includes polyvinyl alcohol or polyvinyl pyrrolidone.

Embodiment 58

The method of embodiment 57, wherein the polymer component comprises
- a liquid having a cellulose-swelling capacity of at least 20 wt. %, present in the polymer component in an amount within the range of 5 wt. % to 70 wt. %; and
- polyvinyl alcohol, present in the polymer component in an amount within the range of 30 wt. % to 95 wt. %.

Embodiment 59

The method of any of embodiments 44-58, wherein the at least one hydrophilic polymer includes a polysaccharide.

Embodiment 60

The method of embodiment 59, wherein the at least one hydrophilic polymer includes an ionic polysaccharide.

Embodiment 61

The method of embodiment 59, wherein the polymer component comprises
- a liquid having a cellulose-swelling capacity of at least 20 wt. %, present in the polymer component in an amount within the range of 5 wt. % to 70 wt. %; and
- one or more saccharides selected from oligosaccharides and polysaccharides, present in the polymer component in a combined about within the range of 30 wt. % to 95 wt. %.

Embodiment 62

The method of embodiment 61, wherein the polymer component comprises one or more polysaccharides selected from starch, alginate, cellulose, hyaluronic acid, chitin, and derivatives thereof.

Embodiment 63

The method or article of any of embodiments 1-62, wherein the polymer component comprises a polysaccharide comprising 1,4-α-linked repeat units according to Formula I:

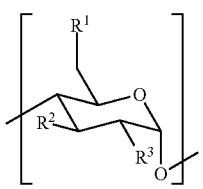

(I)

wherein
- each $R^1$ is selected from hydroxyl, —OR', —OC(O)R', —OR", and an 1,6-α-linked repeat unit according to Formula I;
- $R^2$ and $R^3$ are each independently selected from hydroxyl, —OR', —OC(O)R', and —OR";
- each R' is independently selected from optionally substituted alkyl, cycloalkyl, heterocycloalkyl, aryl, and heteroaryl; and
- each R" is independently selected from nitrate, sulfate, and phosphate.

Embodiment 64

The method or article of any of embodiments 1-63, wherein the polymer component comprises a polysaccharide comprising 1,4β-linked repeat units according to Formulas II and III:

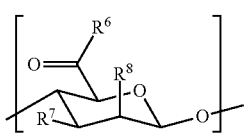

(II)

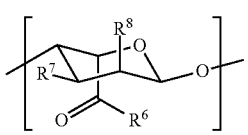

(III)

wherein
- each $R^6$ is independently selected from —OR', —OC(O)R', and —NHR';
- $R^7$ and $R^8$ are each independently selected from —OR', and —OC(O)R', and —OR";
- each R' is independently selected from optionally substituted alkyl, cycloalkyl, heterocycloalkyl, aryl, and heteroaryl; and
- each R" is independently selected from nitrate, sulfate, and phosphate.

Embodiment 625

The method or article of any of embodiments 1-64, wherein the polymer component comprises a polysaccharide comprising 1,4β-linked repeat units according to Formula IV:

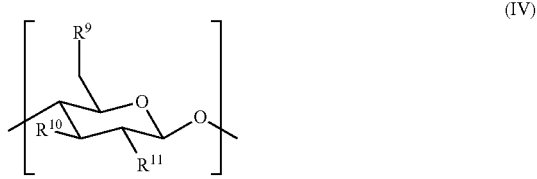

(IV)

wherein
- $R^9$, $R^{10}$, and R" are each independently selected from hydroxyl, —OR', —OC(O)R', and —OR";
- each R' is independently selected from optionally substituted alkyl, cycloalkyl, heterocycloalkyl, aryl, and heteroaryl; and
- each R' is independently selected from nitrate, sulfate, and phosphate.

Embodiment 66

The method or article of any of embodiments 1-65, wherein the polymer component comprises a polysaccharide comprising 1,4β-linked repeat units repeat units according to Formula V:

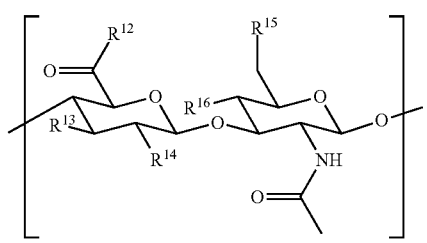

(V)

wherein
- each $R^{12}$ is independently selected from hydroxyl, —OR', —OC(O)R', —NHR', —NHC(O)R', and —OR";
- $R^{13}$, $R^{14}$, $R^{15}$, and $R^{16}$ are each independently selected from hydroxyl, —OR', —OC(O)R', and —OR";
- each R' is independently selected from optionally substituted alkyl, cycloalkyl, heterocycloalkyl, aryl, and heteroaryl; and
- each R" is independently selected from nitrate, sulfate, and phosphate.

Embodiment 67

The method of any of embodiments 61-66, wherein the polymer component comprises one or more ionically cross-linked polysaccharides (e.g., a $Ca^{2+}$-cross-linked polysaccharide).

Embodiment 68

The method of any of embodiments 61-67, wherein none of the polysaccharides of the polymer component comprise a siloxane group.

Embodiment 69

The method of any of embodiments 61-6685, wherein the wherein the liquid comprises (e.g., is) a polar organic solvent selected from methanol, ethanol, acetone, or acetonitrile.

Embodiment 70

The method of any of embodiments 61-68, wherein liquid comprises (e.g., is) water.

Embodiment 71

The method or article of any of embodiments 1-70, wherein the polymer component comprises
one or more polysaccharides, present in the polymer component in a total amount within the range of 10 wt. % to 95 wt. %; and water, present in the polymer component in an amount within the range of 5 wt. % to 90 wt. %.

Embodiment 72

The method or article of any of embodiments 1-70, embodiment wherein the polymer component comprises
one or more polysaccharides, present in the polymer component in a total amount within the range of 30 wt. % to 70 wt. %; and
water, present in the polymer component in an amount within the range of 30 wt. % to 70 wt. %.

Embodiment 73

The method of any one of embodiments 61-72, wherein one or more polysaccharides of the polymer component comprises a plurality of buffering functional groups.

Embodiment 74

The method of any one of embodiments 61-73, wherein the polymer component further comprises one or more active components.

Embodiment 75

The method of embodiment 74, wherein the one or more active components are selected from pharmaceutical compounds, proteins, peptides, cells, or a mixture thereof.

Embodiment 76

The method of any of embodiments 61-75, wherein the polysaccharides, organic solvent, water, and active components are present in a combined amount of at least 80 wt. % (e.g., at least 90 wt. %, or at least 97.5 wt. %) of the polymer component.

Embodiment 77

The method of any of embodiments 44-76, wherein the silicone component and the polymer component are present in a combined amount of at least 80 wt. % (e.g., at least 90 wt. %, or at least 97.5 wt. %) of the hydrophilic polymer composition.

Embodiment 78

The method of any of embodiments 44-77, wherein the silicone component and the polymer component are present in the composition in a dry weight ratio within the range of 95:5 to 40:60 (e.g., 90:10 to 50:50, or 85:15 to 55:45)

Embodiment 79

The method of any of embodiments 44-78, wherein intimately mixing the silicone component and the polymer comprises compounding in a roll mill or a ross mixer.

Embodiment 80

The method of any of embodiments 44-79, further comprising forming the intimate mixture.

Embodiment 81

The method of any one of embodiments 44-70, further comprising curing the intimate mixture.

Embodiment 82

The method of embodiment 81, wherein curing provides cross-links between polysiloxanes.

Embodiment 83

The method of embodiment 81, wherein curing provides cross-links between polysiloxanes and polysaccharides.

Embodiment 84

The method of any of embodiments 81-83, wherein curing comprises heating the intimate mixture to a temperature within the range of 80° C. to 250° C.

Embodiment 85

The method of any of embodiments 81-84, wherein curing comprises irradiating the intimate mixture with actinic radiation.

Embodiment 86

The method of embodiment 85, wherein the actinic radiation has a wavelength of less than 600 nm (e.g., within the range of 200 nm to 300 nm, or 350 nm to 450 nm).

Embodiment 87

A hydrophilic polymer composition made by the method of any of embodiments 44-86.

Embodiment 88

An article according to any of embodiments 1-43, made by the method of any of embodiments 44-86.

We claim:

1. An article having a major exterior surface, the article comprising an intimate mixture of
   a silicone component including at least one polysiloxane, the silicone component comprising the cured product of a curable composition including one or more cross-linkable polysiloxanes and an effective amount of a cross-linking agent; and
   a polymer component including at least one hydrophilic polymer having a water-absorption capacity of at least 50 wt. %;
   wherein the silicone component and the polymer component are present in the mixture in a dry weight ratio within the range of 99.9:0.1 to 30:70.

2. The article of claim 1, wherein the intimate mixture is disposed at the major exterior surface of the article.

3. The article of claim 1, wherein the curable composition includes
   a first polysiloxane having at least about two silicon hydride groups, present in the curable composition in an amount within the range of 0.05 wt. % to 40 wt. %;
   a second polysiloxane having at least about two alkenyl groups, present in the curable composition in an amount within the range of 2 wt. % to 99.95 wt. %; and
   an effective amount of a hydrosilylation catalyst.

4. The article of claim 1, wherein the curable composition includes
   a first polysiloxane having at least about two silicon hydride groups, present in the curable composition in an amount within the range of 1 wt. % to 60 wt. %;
   a second polysiloxane having at least about two alkenyl groups, present in the curable composition in an amount within the range of 20 wt. % to 99.9 wt. %; and
   an effective amount of a hydrosilylation catalyst.

5. The article of claim 1, wherein one or more polysiloxanes of the curable composition comprises at least about one reactive heterocycloalkyl group.

6. The article of claim 1, wherein the silicone component further comprises a filler selected from ceramic particles, glass particles, metallic particles, polymeric particles, or any combination thereof, present in the silicone component in an amount within the range of 1 wt. % to 70 wt. %.

7. The article of claim 1, wherein the polymer component comprises a hydrophilic polymer having a water-absorption capacity of at least 75 wt. %.

8. The article of claim 1, wherein the polymer component comprises a polyvinyl alcohol or a polyvinyl pyrrolidone.

9. The article of claim 1, wherein the polymer component comprises one or more oligosaccharides and/or polysaccharides.

10. The article of claim 9, wherein the polymer component comprises one or more ionic polysaccharides.

11. The article of claim 9, wherein the polymer component comprises one or more polysaccharides selected from starch, alginate, cellulose, hyaluronic acid, chitin, and derivatives thereof.

12. The article of claim 9, wherein the polymer component comprises one or more ionically cross-linked polysaccharides.

13. The article of claim 1, wherein one or more polysiloxanes of the silicone component is cross-linked via covalent bonding to a hydrophilic polymer of the polymer component.

14. The article of claim 1, wherein the intimate mixture further comprises a liquid having a cellulose-swelling capacity of at least 20 wt. %.

15. The article of claim 1, wherein the intimate mixture further comprises water.

16. The article of claim 15, wherein the weight ratio of the combined amount of hydrophilic polymers to water in the intimate mixture is within the range of 10:90 to 95:5.

17. The article of claim 15, wherein an exterior surface of the article comprises a hydrogel formed from the water and the one or more hydrophilic polymers.

18. The article of claim 1, wherein the intimate mixture further comprises a polar organic solvent selected from methanol, ethanol, acetone, or acetonitrile.

19. The article of claim 1, wherein one or more hydrophilic polymers of the polymer component comprises a plurality of buffering functional groups.

20. The article of claim 1, wherein the exterior surface further comprises one or more active components selected from pharmaceutical compounds, proteins, peptides, cells, or a mixture thereof.

21. The article of claim 1, wherein the intimate mixture is formed as a layer on a substrate.

22. The article of claim 1, in the form of a tubular article.

23. The article of claim 1, in the form of a catheter, wound dressing or beverage tube.

24. A method for preparing a hydrophilic polymer composition, the method comprising intimately mixing
    a silicone component including at least one polysiloxane; and
    a polymer component including at least one hydrophilic polymer having a water-absorption capacity of at least 50 wt. %;
    wherein the silicone component and the polymer component are present in the composition in a dry weight ratio within the range of 99.9:0.1 to 30:70.

25. The article of claim 1, wherein the intimate mixture of the silicone component and the polymer component is made by a method comprising intimately mixing the polymer component with a curable composition including one or more cross-linkable polysiloxanes and an effective amount of a cross-linking agent, and then curing the curable composition.

26. The article of claim 1, wherein the silicone component and the polymer component are present in the composition in a dry weight ratio within the range of 95:5 to 30:70.

27. An article having a major exterior surface, the article comprising an intimate mixture of
    a silicone component including at least one polysiloxane; and
    a polymer component including at least one hydrophilic polymer having a water-absorption capacity of at least 50 wt. %, the polymer component comprising one or more polysaccharides selected from starch, alginate, cellulose, hyaluronic acid, chitin, and derivatives thereof;
    wherein the silicone component and the polymer component are present in the mixture in a dry weight ratio within the range of 99.9:0.1 to 30:70.

* * * * *